(12) United States Patent
Kashima et al.

(10) Patent No.: US 11,642,004 B2
(45) Date of Patent: May 9, 2023

(54) IMAGE PROCESSING DEVICE, IMAGE PROCESSING METHOD AND RECORDING MEDIUM

(71) Applicant: Sony Corporation, Tokyo (JP)

(72) Inventors: Koji Kashima, Kanagawa (JP); Tsuneo Hayashi, Tokyo (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 17/026,324

(22) Filed: Sep. 21, 2020

(65) Prior Publication Data

US 2021/0007576 A1 Jan. 14, 2021

Related U.S. Application Data

(63) Continuation of application No. 16/071,299, filed as application No. PCT/JP2017/004107 on Feb. 3, 2017, now Pat. No. 10,799,088.

(30) Foreign Application Priority Data

Mar. 9, 2016 (JP) .............................. JP2016-045244

(51) Int. Cl.
*G06T 7/00* (2017.01)
*A61B 1/00* (2006.01)
*G02B 5/30* (2006.01)

(52) U.S. Cl.
CPC .... *A61B 1/000095* (2022.02); *A61B 1/00043* (2013.01); *G02B 5/3083* (2013.01); *G06T 7/0012* (2013.01)

(58) Field of Classification Search
CPC ... A61B 1/00009; A61B 1/00043; A61B 3/00; G02B 5/3083; G06T 7/0012

USPC .......................................................... 382/254
See application file for complete search history.

(56) References Cited

U.S. PATENT DOCUMENTS

| | | |
|---|---|---|
| 2006/0103592 A1 | 5/2006 | Tanaka et al. |
| 2012/0281280 A1 | 11/2012 | Buehler et al. |
| 2014/0176692 A1 | 6/2014 | Tsuyuki et al. |
| 2014/0185922 A1 | 7/2014 | Isogawa |
| 2014/0293117 A1 | 10/2014 | Murakami et al. |
| 2014/0362332 A1 | 12/2014 | Buehler et al. |

(Continued)

FOREIGN PATENT DOCUMENTS

| | | |
|---|---|---|
| EP | 2 868 254 A1 | 5/2015 |
| JP | 8-37604 A | 2/1996 |
| JP | 10-165365 A | 6/1998 |

(Continued)

OTHER PUBLICATIONS

Japanese Office Action dated Jul. 7, 2020, in corresponding Japanese Patent Application 2016-045244.

(Continued)

*Primary Examiner* — Amandeep Saini
(74) *Attorney, Agent, or Firm* — Xsensus LLP

(57) ABSTRACT

A medical imaging system having an image sensor, a birefringent mask coupled to the image sensor, and processing circuitry that obtains image data from the image sensor, and performs processing on the image data based on unique optical characteristics of a coupled medical device, wherein the processing includes selecting at least one of depth of field expansion and blur improvement based on the unique optical characteristics.

13 Claims, 20 Drawing Sheets

(56) References Cited

U.S. PATENT DOCUMENTS

2017/0262976 A1* 9/2017 Choi .................. A61B 6/4233

FOREIGN PATENT DOCUMENTS

| | | |
|---|---|---|
| JP | 10-290780 A | 11/1998 |
| JP | 11-183809 A | 7/1999 |
| JP | 2000-5127 A | 1/2000 |
| JP | 2002-045354 A | 2/2002 |
| JP | 2006-024796 A | 1/2006 |
| JP | 2006-210917 A | 8/2006 |
| JP | 2010-051350 A | 3/2010 |
| JP | 2010-68992 A | 4/2010 |
| JP | 2011072530 A | 4/2011 |
| JP | 2011193983 A | 10/2011 |
| JP | 2012-135345 A | 7/2012 |
| JP | 2012-217579 A | 11/2012 |
| JP | 2014-233533 A | 12/2014 |
| WO | WO 2011/045065 A1 | 4/2011 |
| WO | WO-2011045065 A1 * | 4/2011 ......... G02B 27/0075 |
| WO | WO 2013/081086 A1 | 6/2013 |
| WO | 2014/050191 A1 | 4/2014 |
| WO | WO 2014/050191 A1 | 4/2014 |
| WO | 2016/098282 A1 | 6/2016 |

OTHER PUBLICATIONS

Japanese Office Action dated Jan. 21, 2020 in Japanese Application 2016-045244.
International Search Report dated May 10, 2017 in PCT/JP2017/004107, 4 pages.
Office Action (Decision of Dismissal of Amendment) dated Dec. 15, 2020, in corresponding Japanese patent Application No. 2016-045244, 4 pages.

* cited by examiner

Fig. 3
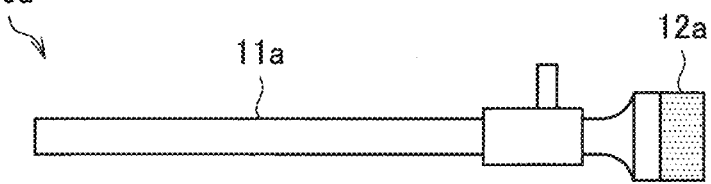
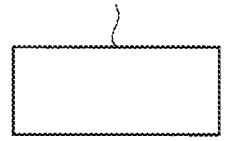
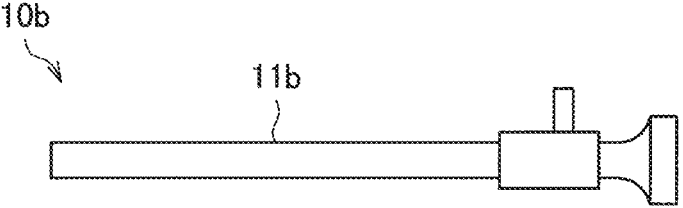
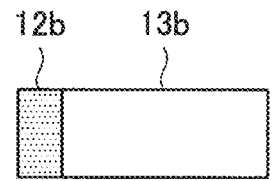
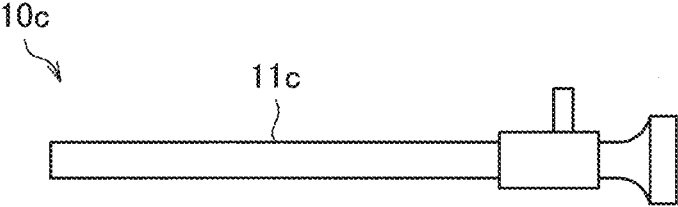
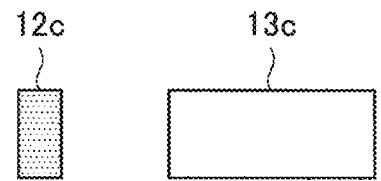

Fig. 16
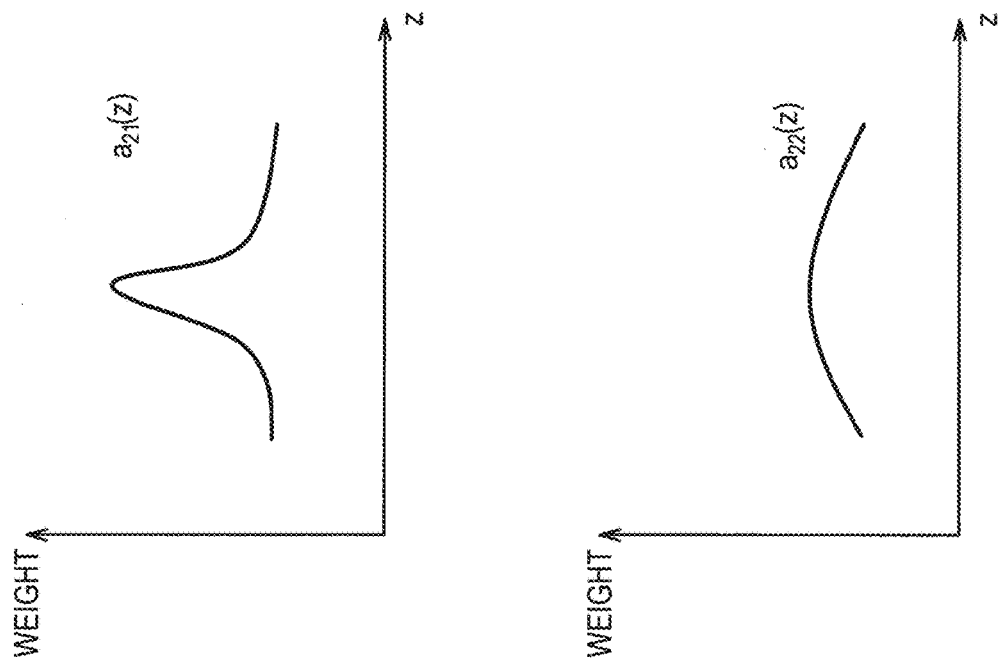
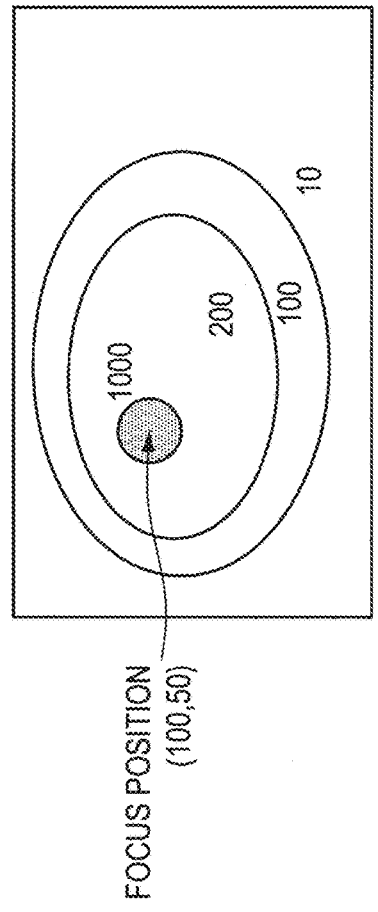
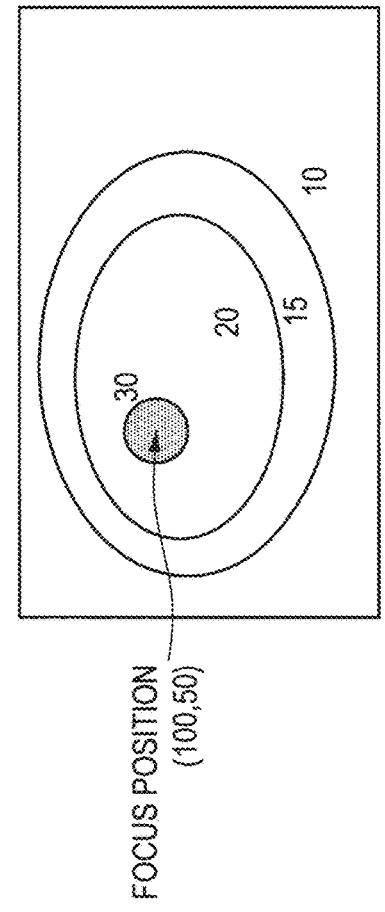

IMAGE PROCESSING DEVICE, IMAGE PROCESSING METHOD AND RECORDING MEDIUM

CROSS REFERENCE TO RELATED APPLICATIONS

This application is a continuation of U.S. application Ser. No. 16/071,299, filed Jul. 19, 2018, which is based on PCT filing PCT/JP2017/004107, filed Feb. 3, 2017, which claims the benefit of Japanese Priority Patent Application JP 2016-045244, filed Mar. 9, 2016, the entire contents of each are incorporated herein by reference.

TECHNICAL FIELD

The present disclosure relates to an image processing device, an image processing method and a recording medium.

BACKGROUND ART

In recent years, due to the development of surgical techniques and surgical instruments, surgeries (so-called microsurgeries) for performing various treatments while medical observation devices such as a surgical microscope or an endoscope are used to observe affected parts have been frequently performed. In addition, not only such devices capable of optically observing affected parts but also devices configured to display images of affected parts that are captured by an imaging device (a camera) or the like on a display device such as a monitor as electronic images are proposed. For example, in PTL 1, an example of a so-called electronic endoscope system that can display images of affected parts that are captured by an imaging device on a display unit is disclosed.

CITATION LIST

Patent Literature

[PTL 1]
JP 2002-45354A

SUMMARY

Technical Problem

Incidentally, in an imaging device applied to a medical observation device, according to a characteristic of an optical system (for example, an endoscope) for forming a subject image on an imaging element, so-called blur may occur in a captured image. In such a situation, a focus point does not match a part of a subject and observation of the subject is difficult, and for example, it may be necessary to rematch a focus point with respect to the subject. Therefore, in such a situation, it is necessary to provide, for example, a mechanism through which it is possible to acquire an image having a higher depth of field in some cases.

In addition, in the field of medical care, due to differences of observation environments when so-called special light observation is performed, differences of observation targets such as samples or affected parts, and differences of observation methods according to surgical procedures of surgeries (in other words, differences of observation modes and observation scenes), conditions for observing a subject image may differ. In such a situation, characteristics necessary for an acquired subject image, for example, a breadth of an observation range such as a depth of field and an amount of blur (in other words, a sense of resolution), may differ.

Therefore, the present disclosure proposes an image processing device, an image processing method and a recording medium through which it is possible to observe a subject image in a more suitable manner according to a state and situation related to observation of the subject image.

Solution to Problem

According to an embodiment of the present disclosure there is described a medical imaging system. The system including an image sensor, a birefringent mask coupled to the image sensor, and processing circuitry configured to obtain image data from the image sensor, perform processing on the image data based on unique optical characteristics of a coupled medical device, wherein the processing includes selecting at least one of depth of field expansion and blur improvement based on the unique optical characteristics.

According to an embodiment of the present disclosure there is described a medical image processing apparatus. The medical image processing apparatus includes processing circuitry configured to obtain image data from an image sensor having a birefringent mask coupled thereto, perform processing on the image data based on unique optical characteristics of a coupled medical device, wherein the processing includes at least one of depth of field expansion and blur improvement based on the unique optical characteristics.

According to an embodiment of the present disclosure there is described a medical image processing method. The medical image processing method includes the steps of obtaining image data from an image sensor having a birefringent mask coupled thereto, performing processing on the image data based on unique optical characteristics of a coupled medical device, the processing including at least one of depth of field expansion and blur improvement based on the unique optical characteristics, and outputting the generated images.

Advantageous Effects of Invention

According to an embodiment of the present disclosure described above, there are provided an image processing device, an image processing method and a recording medium through which it is possible to observe a subject image in a more suitable manner according to a state and situation related to observation of the subject image.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 3 is an explanatory diagram for describing an example of a configuration of the endoscopic device according to the embodiment.

FIG. 16 is an explanatory diagram for describing an example of control related to calculating PSF information in an image processing device according to Example 2-1.

DESCRIPTION OF EMBODIMENTS

Figure 1:
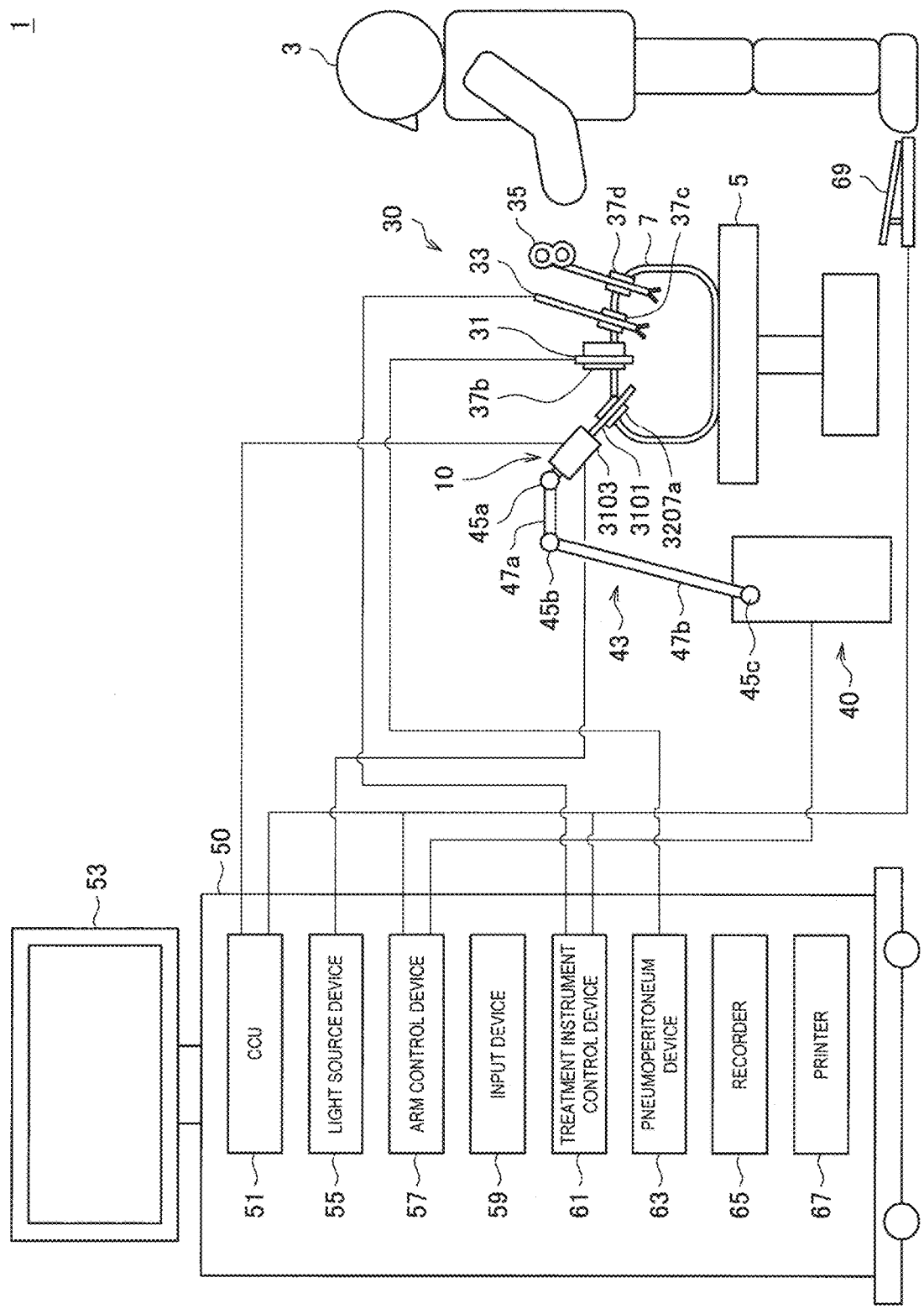
FIG. 1 is an explanatory diagram for describing an example of a schematic configuration of an endoscopic device according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.
1. System overview
2. Configuration of optical element
3. Restoration processing
3.1. Configuration of image processing device
3.2. Process of image processing device
4. Examples
4.1. Example 1: Acquisition of PSF information for each instrument
4.2. Example 2: Example of calculating PSF information according to various conditions
5. Hardware configuration
6. Conclusion

1. SYSTEM OVERVIEW

First, an overview of an exemplary system to which a technology according to the present disclosure may be applied will be described. FIG. 1 shows an example of a schematic configuration of a medical image processing system 1 according to an embodiment. The medical image processing system 1 is an endoscopic surgery system. In the example of FIG. 1, a surgeon (doctor) 3 uses the medical image processing system 1 and performs endoscopic surgery on a patient 7 in a patient bed 5. The medical image processing system 1 includes an endoscope 10, another surgical instrument (a surgical tool) 30, a support arm device 40 configured to support the endoscope 10, and a cart 50 in which various devices for endoscopic surgery are mounted.

In the endoscopic surgery, instead of laparotomy through which an abdominal wall is incised, an abdominal wall is punctured by a plurality of cylindrical opening instruments 37a to 37d called trocars. Then, a lens barrel 11 of the endoscope 10 and the surgical tool 30 are inserted into a body cavity of the patient 7 through the trocars 37a to 37d. In the example of FIG. 1, as the surgical tool 30, a pneumoperitoneum tube 31, an energy treatment instrument 33 and a forceps 35 are shown. The energy treatment instrument 33 is used for treatments such as incision or exfoliation of tissues or suturing of blood vessels using a high frequency current or ultrasonic vibration. However, the shown surgical tool 30 is only an example. Another type of a surgical tool (for example, tweezers or a retractor) may be used.

An image of the body cavity of the patient 7 captured by the endoscope 10 is displayed by a display device 53. The surgeon 3 uses the energy treatment instrument 33 and the forceps 35 to perform a treatment, for example, resecting an affected part, while viewing a display image in real time. Although not shown, the pneumoperitoneum tube 31, the energy treatment instrument 33 and the forceps 35 are supported by a user such as the surgeon 3 or an assistant during surgery.

The support arm device 40 includes an arm portion 43 that extends from a base portion 41. In the example of FIG. 1, the arm portion 43 includes joint portions 45a, 45b and 45c and links 47a and 47b, and supports the endoscope 10. The arm portion 43 is driven according to control from an arm control device 57. As a result, a position and an orientation of the endoscope 10 are controlled and the position of the endoscope 10 may be stably fixed.

The endoscope 10 includes the lens barrel 11 and a camera head 13 that is connected to a base end of the lens barrel 11. A part up to a certain length from a distal end of the lens barrel 11 is inserted into the body cavity of the patient 7. While the endoscope 10 is configured as a so-called rigid endoscope including the rigid lens barrel 11 in the example of FIG. 1, the endoscope 10 may be configured as a flexible endoscope.

An opening into which an objective lens is fitted is provided at the distal end of the lens barrel 11. A light source device 55 is connected to the endoscope 10. Light generated from the light source device 55 is guided to the distal end of the lens barrel by a light guide that extends to an inside of the lens barrel 11 and is emitted toward an observation target in the body cavity of the patient 7 through the objective lens. Alternatively, the endoscope 10 may be a direct-view endoscope, a perspective view endoscope or a side view endoscope.

The camera head 13 includes an illumination unit and an imaging unit that includes an optical system, a drive system and an image sensor therein. The illumination unit emits illumination light supplied through a light guide from the light source device 55 toward a subject. The optical system generally includes a lens unit and collects observation light (reflected light of illumination light) from the subject captured from the distal end of the lens barrel 11 onto the image sensor. Positions of a zoom lens and a focus lens in the lens unit may be changed when the drive system is driven in order to variably control imaging conditions such as a magnification and a focal length. The image sensor of the camera head 13 performs photoelectric conversion of the observation light collected by the optical system and generates an image signal that is an electrical signal. The image sensor may be a three-plate type sensor including separate imaging elements that generate image signals of three color components or may be an image sensor of another type such as a single-plate type or a two-plate type. The image sensor may include any type of imaging element, for example, a complementary metal oxide semiconductor (CMOS) and a charge-coupled device (CCD). The image signal generated by the image sensor is transmitted to a camera control unit (CCU) 51 as RAW data.

In certain embodiments, a captured image represented by the image signal generated by the camera head 13 includes a parallax determination image. The parallax determination image generally includes a right eye image and a left eye image. The right eye image and the left eye image may be generated by a right eye image sensor and a left eye image sensor of a compound eye camera, respectively. Alternatively, the right eye image and the left eye image may be generated by a single image sensor of a monocular camera (for example, using a shutter switching method).

The CCU 51 is connected to the camera head 13 through a signal line and a communication interface. The signal line between the camera head 13 and the CCU 51 is a high speed transmission line through which two-way communication is possible, for example, an optical cable. The CCU 51 includes a processor such as a central processing unit (CPU) and a memory such as a random access memory (RAM) and controls overall operations of the endoscope 10 and the display device 53. The CCU 51 may further include a frame memory for temporarily storing an image signal and at least one graphics processing unit (GPU) for performing image processing. For example, the CCU 51 determines parallax for each pixel (or other unit) based on the parallax determination image input from the camera head 13. The determined parallax may be used for image processing, for example, generating a stereoscopic image, increasing a depth of field, emphasizing a stereoscopic sense or extending a dynamic range. The CCU 51 may output an image generated as an image processing result to the display device 53 for displaying or a recorder 65 for recording. A series of output images may form a moving image (a video). The image processing performed in the CCU 51 may include general processing, for example, development and noise reduction. In addition, the CCU 51 transmits a control signal to the camera head 13 and controls driving of the camera head 13. The control signal may include, for example, information for designating the above-described imaging conditions.

The display device 53 displays a stereoscopic image based on an input display image signal under control of the CCU 51. The display device 53 may display the stereoscopic image using any of methods such as an active shutter method, a passive method and a glass-less method.

The light source device 55 includes, for example, an LED, a xenon lamp, a halogen lamp, a laser light source, or a light source including a combination thereof, and supplies illumination light to be emitted toward the observation target to the endoscope 10 through a light guide.

The arm control device 57 includes a processor, for example, a CPU, and is operated according to a predetermined program and thus controls driving of the arm portion 43 of the support arm device 40.

An input device 59 includes at least one input interface through which a user input to the medical image processing system 1 is received. The user can input various pieces of information or input various instructions to the medical image processing system 1 through the input device 59. For example, the user may input setting information or other parameters to be described below through the input device 59. In addition, for example, the user may input an instruction for driving the arm portion 43, an instruction for changing imaging conditions (for example, a type of illumination light, a magnification and a focal length) in the endoscope 10 or an instruction for driving the energy treatment instrument 33 through the input device 59.

The input device 59 may process any type of user input. For example, the input device 59 may detect a physical user input through a mechanism such as a mouse, a keyboard, a switch (for example, a foot switch 69) or a lever. The input device 59 may detect a touch input through a touch panel. The input device 59 may be implemented in the form of a wearable device such as an eyeglass-type device or a head mounted display (HMD) and may detect a line of sight or a gesture of the user. In addition, the input device 59 may include a microphone capable of collecting voice of the user and detect a voice command through the microphone.

A treatment instrument control device 61 controls driving of the energy treatment instrument 33 in order to perform treatments such as ablation or incision of tissues or suturing of blood vessels. A pneumoperitoneum device 63 sends a gas into the body cavity through the pneumoperitoneum tube 31 in order to inflate the body cavity of the patient 7 so that a field of view that is observed by the endoscope 10 is ensured and a work space of a surgeon is ensured. The recorder 65 records various pieces of information about operations for medical care (for example, at least one of setting information, image information and measurement information obtained from a vital sensor (not shown)) in a recording medium. A printer 67 prints the various pieces of information about operations for medical care in any format of text, an image and a graph.

The endoscope 10 according to the present embodiment may have a configuration in which an optical element 12 such as a so-called optical mask is insertable between the lens barrel 11 and the camera head 13. Examples of the optical element 12 include a birefringent mask (BM) and a cubic phase mask. In the medical image processing system 1 according to the present embodiment, when the optical element 12 is interposed between the lens barrel 11 and the camera head 13, optical characteristics of a series of optical systems configured to form an image of the subject on the imaging element in the camera head 13 are changed, and an amount of blur in the captured image is adjusted (for example, a depth of field is controlled). The optical element 12 will be separately described below in detail.

An overview of an exemplary system to which a technology according to the present disclosure may be applied has been described above with reference to FIG. 1.

2. CONFIGURATION OF OPTICAL ELEMENT

Next, characteristics of the optical element 12 that is inserted between the lens barrel 11 and the camera head 13 in the endoscope 10 according to the present embodiment will be described in detail with reference to FIG. 2 to FIG. 6.

In recent years, imaging elements (so-called image sensors) used in an imaging device such as a camera which have resolutions that tend to become higher and are not limited to "HD (1280×720)" but also have "4K UHD (3840×2160)" and "8K UHD (7680×4320)" have also been proposed. Therefore, a high resolution of the captured image is desirable for a medical observation device such as the endoscope 10 according to the present embodiment. On the other hand, a pixel size of the imaging element tends to be smaller with a higher resolution, and a light intensity of light that is collected at each pixel tends to be relatively smaller. In such a situation, for example, when an aperture is more open (that is, an F value is set to be smaller), the lack of light intensity may be compensated for. However, due to the opening of the aperture, a depth of field may become narrower. In view of the above situation, the endoscope 10 according to the present embodiment has a configuration in which the optical element 12 is insertable between the lens barrel 11 and the camera head 13 as described above and a depth of field of the captured image is controlled when the optical element 12 is inserted.

Figure 2:
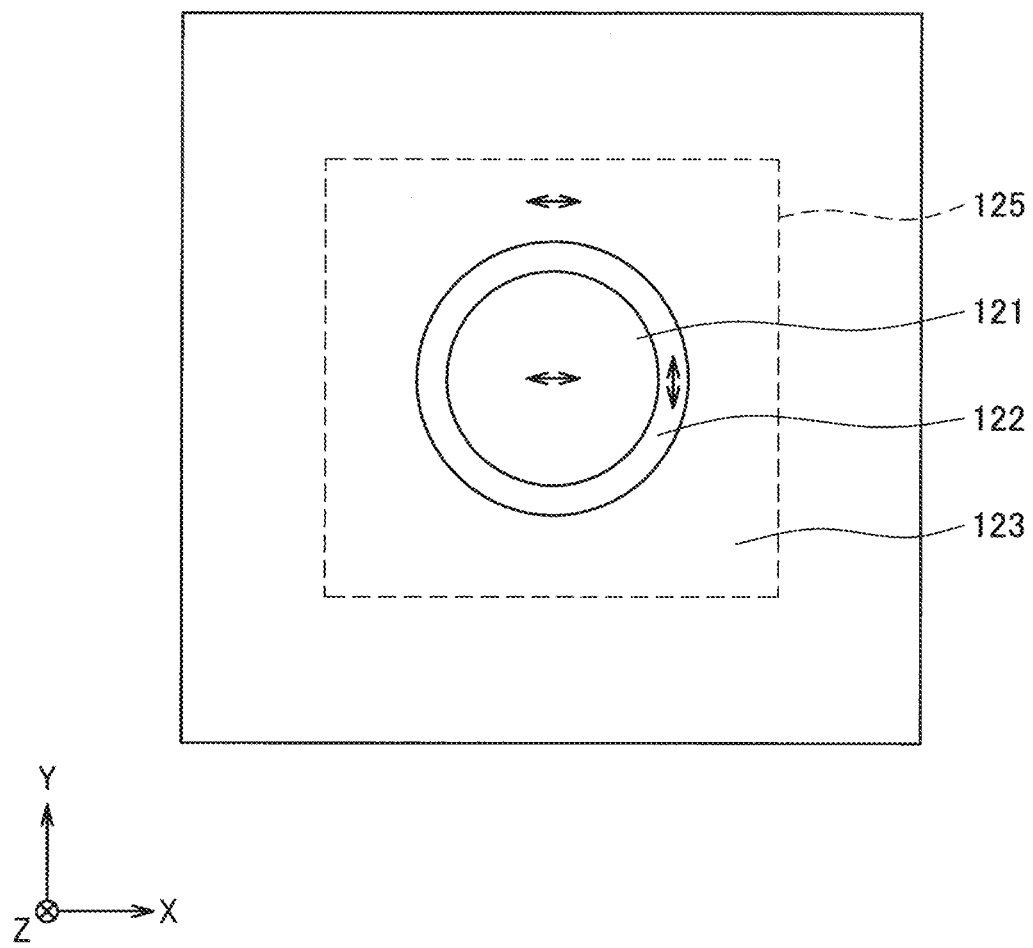
FIG. 2 is an explanatory diagram for describing an example of a schematic configuration of an optical element that is applied to an endoscopic device according to the embodiment.

For example, FIG. 2 is an explanatory diagram for describing an example of a schematic configuration of the optical element 12 that is applied to the endoscope 10 according to the present embodiment. Specifically, FIG. 2 shows an example in which the optical element 12 is configured as a birefringent mask and shows an example of a configuration of the optical element 12 when the optical element 12 is viewed in an optical axis direction of the camera head. In FIG. 2, in the drawing, a lateral direction is defined as an x direction, a longitudinal direction is defined as a y direction and a depth direction (that is, the optical axis direction of the camera head 13) is defined as a z direction. In the following description, when there is no particular definition, the optical axis direction (in other words, the depth direction) of an imaging device (for example, an imaging device 3) is defined as the z direction, and the lateral direction and the longitudinal direction (that is, a direction perpendicular to an optical axis) of an image captured by the imaging device are defined as the x direction and the y direction, respectively.

As shown in FIG. 2, in the optical element 12, in an inside of an area indicated by a reference sign 125, a plurality of polarizing elements 121 to 123 are arranged toward the outside from the vicinity of the center of the area 125. As a more specific example, in the example shown in FIG. 2, in the optical element 12, the plurality of polarizing elements 121 to 123 are concentrically arranged on an xy plane perpendicular to the optical axis. Arrows shown in FIG. 2 schematically indicate polarizing directions of polarizing elements to which the arrows are assigned. That is, the polarizing elements 121 to 123 are set such that polarizing directions of adjacent polarizing elements are set to be different from each other.

For example, in the example shown in FIG. 2, a polarizing direction of the polarizing element 121 is the x direction. On the other hand, a polarizing direction of the polarizing element 122 that is adjacent to the polarizing element 121 is the y direction that is a direction rotated 90 degrees from the polarizing direction (the x direction) of the polarizing element 121. Similarly, a polarizing direction of the polarizing element 123 that is adjacent to the polarizing element 122 is the x direction that is a direction rotated 90 degrees from the polarizing direction (the y direction) of the polarizing element 122.

In such a configuration, light collected by the lens barrel 11 is incident on any of the polarizing elements 121 to 123 of the optical element 12 according to a position on the xy plane perpendicular to the optical axis (the z direction) and the light polarized by the polarizing element is incident on the camera head 13.

As long as the optical element 12 can be interposed between the lens barrel 11 and the camera head 13, the configuration of the endoscope 10 is not particularly limited. For example, FIG. 3 is an explanatory diagram for describing an example of a configuration of the endoscope 10 according to the present embodiment and shows an example of a configuration for interposing the optical element 12 between the lens barrel 11 and the camera head 13.

As a specific example, a configuration example of an endoscope indicated by a reference sign 10a is an example in which the optical element 12 is configured as a part of the lens barrel 11. Specifically, in the endoscope 10a, an optical element 12a is held at an end side that will be installed at a camera head 13a within the lens barrel 11a. In such a configuration, light collected by the lens barrel 11a passes through the optical element 12a when it is emitted to the outside of the lens barrel 11a and the light that has passed through the optical element 12a is incident on the camera head 13a. In such a configuration, it is possible to perform a depth of field increasing process optimal for the endoscope.

In addition, as another example, a configuration example of an endoscope indicated by a reference sign 10b is an example in which the optical element 12 is configured as a part of the camera head 13. Specifically, in the endoscope 10b, the optical element 12b is held at an end side that will be installed at a lens barrel 11b within a camera head 13b. In such a configuration, light collected by the lens barrel 11b passes through the optical element 12b when it is incident on the camera head 13b. In such a configuration, it is possible to perform the depth of field increasing process using an endoscope of the related art in addition to a dedicated endoscope.

In addition, a configuration example of an endoscope indicated by a reference sign 10c is an example in which the optical element 12 is configured as a so-called attachment. Specifically, the optical element 12 has a configuration that is detachable with respect to a lens barrel 11c and a camera head 13c and is interposed between the lens barrel 11c and the camera head 13c. In such a configuration, when an optical element 12c is installed to be interposed between the lens barrel 11c and the camera head 13c, light collected by the lens barrel 11c passes through the optical element 12c and is then incident on the camera head 13c. Since such a configuration can support various endoscopes and camera heads, it can be easily adopted.

It should be noted that the configuration examples shown in FIG. 3 are only examples. As long as the optical element 12 can be interposed between the lens barrel 11 and the camera head 13, the configuration of the endoscope 10 is not limited to the configuration examples shown in FIG. 3.

Figure 4:
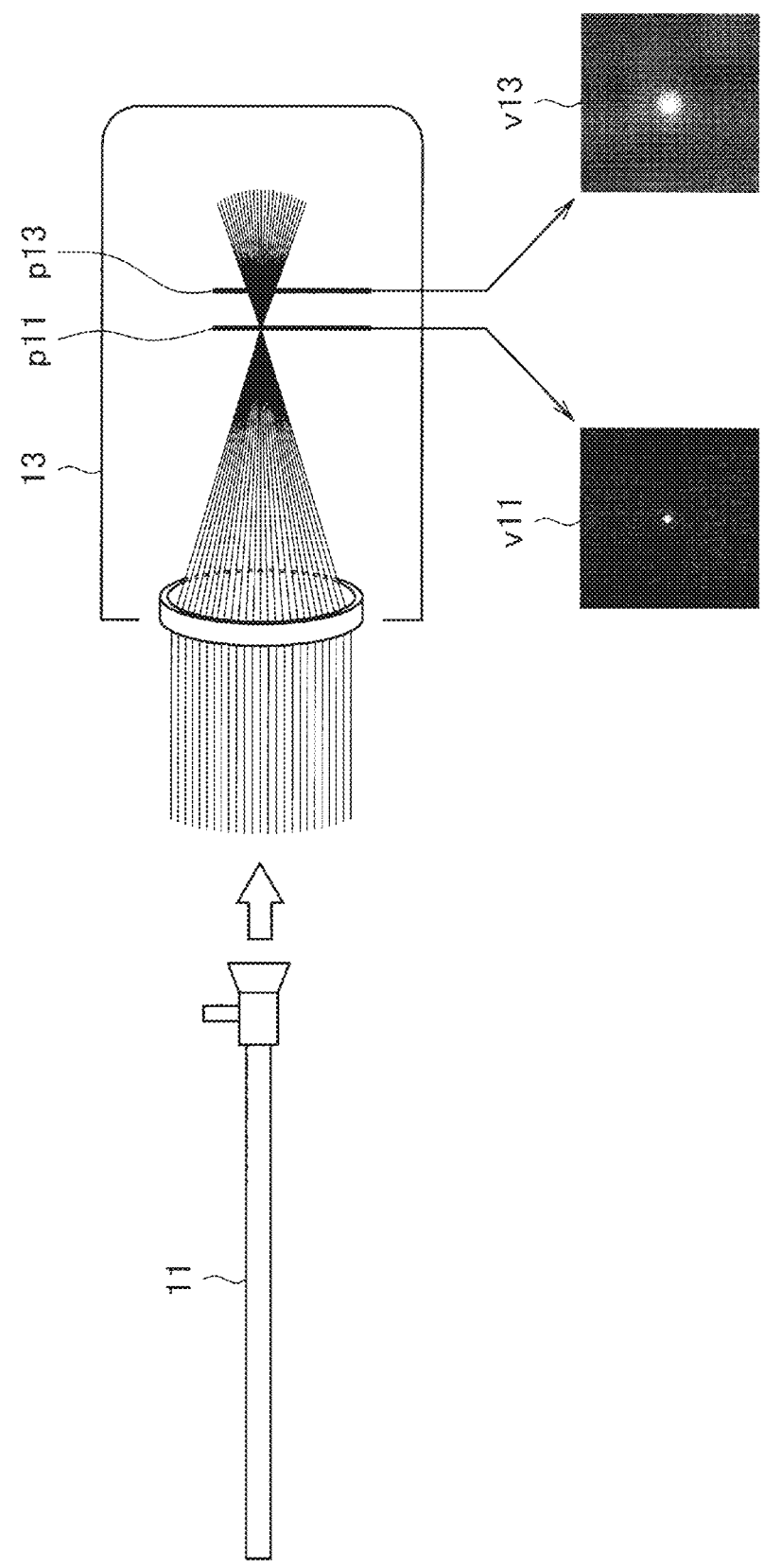
FIG. 4 is an explanatory diagram for describing a characteristic of the optical element according to the embodiment.
Figure 5:
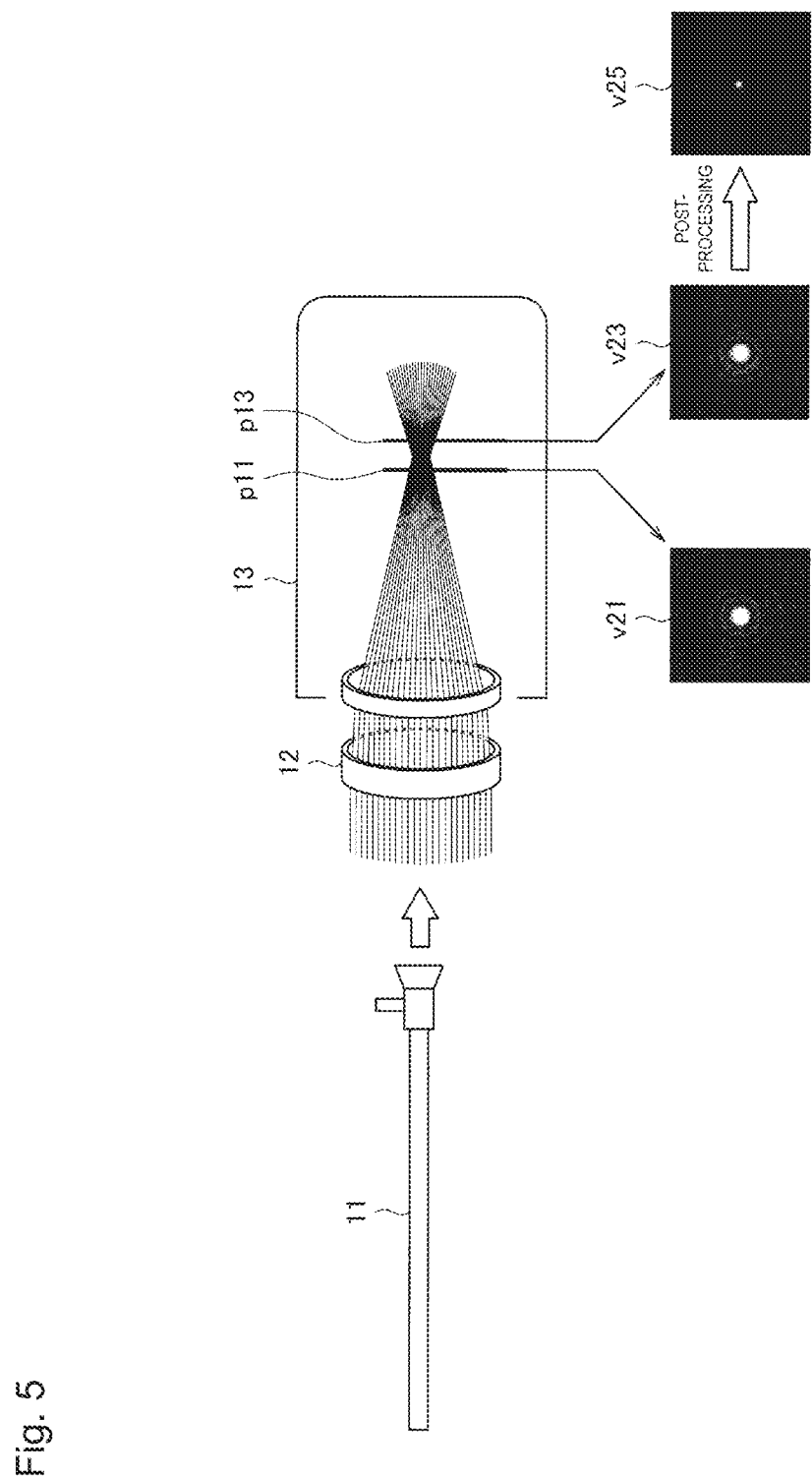
FIG. 5 is an explanatory diagram for describing a characteristic of the optical element according to the embodiment.

Here, characteristics of the optical element 12 shown in FIG. 2 will be described with reference to FIG. 4 and FIG. 5. FIG. 4 and FIG. 5 are explanatory diagrams for describing characteristics of the optical element 12 according to the present embodiment. Specifically, FIG. 4 is an example in which the optical element 12 is not interposed between the lens barrel 11 and the camera head 13 and schematically shows an optical path of light that is collected by the lens barrel 11 and guided to the camera head 13. In addition, FIG. 5 is an example in which the optical element 12 is interposed between the lens barrel 11 and the camera head 13 and schematically shows an optical path of light that is collected by the lens barrel 11 and guided to the camera head 13 through the optical element 12.

In the example shown in FIG. 4, the optical path of the light that is collected by the lens barrel 11 and guided to the camera head 13 is controlled to form an image on an image plane of the imaging element by an image forming optical system of the camera head 13. In FIG. 4, an image indicated by a reference sign v11 schematically shows a subject image that is formed at a position indicated by a reference sign p11. In addition, an image indicated by a reference sign v13 schematically shows a subject image that is formed at a position indicated by a reference sign p13.

On the other hand, in the example shown in FIG. 5, light collected by the lens barrel 11 is guided to the camera head 13 through the optical element 12 and an optical path thereof is controlled by the image forming optical system of the camera head 13. In FIG. 5, an image indicated by a reference sign v21 schematically shows a subject image that is formed at a position indicated by the reference sign p11. In addition, an image indicated by a reference sign v23 schematically shows a subject image that is formed at a position indicated by the reference sign p13.

Comparing FIG. 4 and FIG. 5, when the optical element 12 is inserted, characteristics of a series of optical systems configured to form a subject image on the imaging element of the camera head 13 (hereinafter simply referred to as "a series of optical systems") are changed. Specifically, when the optical element 12 is inserted, a change in a shape (that is, a point spread function (PSF)) of the formed subject image between the position p11 and the position p13 is small compared to when the optical element 12 is not inserted.

Figure 6:
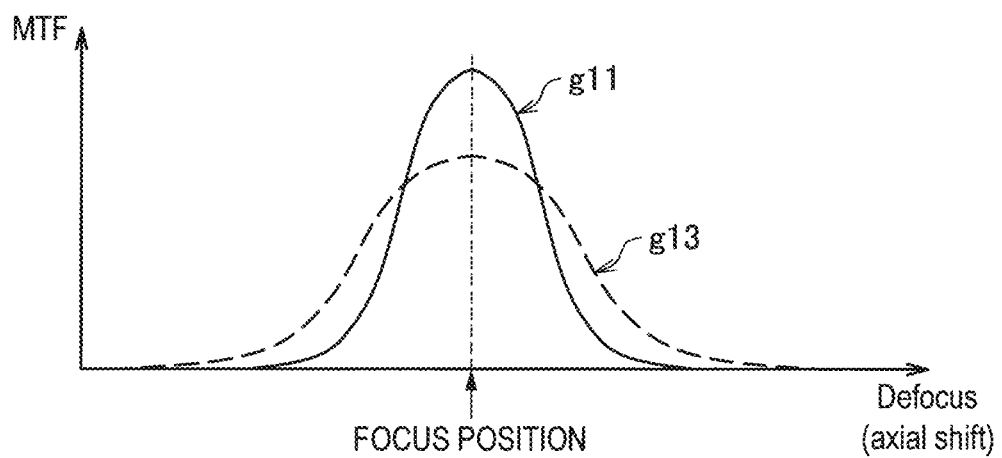
FIG. 6 is an explanatory diagram for describing an example of a characteristic of the optical element that is applied to the endoscopic device according to the embodiment.

For example, FIG. 6 is an explanatory diagram for describing an example of a characteristic of the optical element 12 that is applied to the endoscope 10 according to the present embodiment and shows an example of a change of a modulation transfer function (MTF) of the series of optical systems in which the optical element 12 is inserted. In FIG. 6, a horizontal axis represents a deviation (that is, an amount of defocus) in the optical axis direction using an image forming plane (in other words, a focus position) of a series of optical systems as a reference and a vertical axis represents the modulation transfer function (MTF). In addition, in FIG. 6, a graph indicated by a reference sign g11 shows an example of the modulation transfer function (MTF) of the series of optical systems in which the optical element 12 is not interposed between the lens barrel 11 and the camera head 13 as shown in FIG. 4. In addition, a graph indicated by a reference sign g13 shows an example of the modulation transfer function (MTF) of the series of optical systems in which the optical element 12 is inserted between the lens barrel 11 and the camera head 13 as shown in FIG. 5.

As shown in FIG. 6, compared to when the optical element 12 is not applied, when the optical element 12 is applied, characteristics of the series of optical systems are changed so that the modulation transfer function (MTF) is distributed across a wider range in the optical axis direction. That is, when the optical element 12 is applied, it is possible to further increase a depth of field.

On the other hand, as can be seen from FIG. 6, when the optical element 12 is applied, a value of the modulation transfer function (MTF) at the focus position decreases compared to when the optical element 12 is not applied. Here, in the medical image processing system 1 according to the present embodiment, as shown in FIG. 5, when restoration processing (image processing) is performed on the image captured by the camera head 13, the image is restored to reduce deterioration (so-called blur) of the subject image that occurs when a value of the modulation transfer function (MTF) decreases. For example, in FIG. 5, an image indicated by a reference sign v25 shows an example of a subject image on which the restoration processing has been performed when the restoration processing is performed on the subject image v23. According to such control, for example, a depth of field increases and it is possible to obtain an image in which the observation target is more clearly presented (that is, a sharper image).

In addition, when a sample is observed using a medical observation device such as an endoscopic device or a so-called surgical microscope, conditions in which the sample is observed (in other words, conditions necessary for an image of the sample) may be assumed to differ according to differences in observation environments, observation targets and observation methods. As a specific example, in surgery to approach deep portions of the nose, ear and brain, since the surgical field is long and narrow, it is necessary to acquire an image having a broader depth of field in some cases. In addition, as another example, in surgery in which a finer procedure is necessary, for example, in a case in which a treatment is performed on a blood vessel on a surface of the brain, it is necessary to acquire an image whose sense of resolution is better even if a depth of field is somewhat shallow.

In view of such a situation, in the medical image processing system 1 according to the present embodiment, content of the restoration processing is controlled according to conditions related to observation of the sample, for example, ranges of a wavelength of a light component serving as an observation target, an image height (in other words, an area in an image) and the depth direction (that is, the optical axis direction) (hereinafter these are generally referred to as an "observation range"), an observation environment, an observation target and an observation method (for example, an observation mode). In such a configuration, the medical image processing system 1 according to the present embodiment can acquire an image in which the observation target can be observed in a more suitable manner according to, for example, conditions of the observation environment when so-called special light observation is performed and characteristics (for example, a distribution of color components and a distribution of luminance) of a subject (that is, for example, a sample or an affected part) serving as the observation target. Details of the restoration processing (image processing) will be separately described below in connection with an example of a functional configuration of an image processing device (that is, a configuration of a part that performs image processing within the CCU 51 in FIG. 1).

The characteristic of the optical element 12 that is inserted between the lens barrel 11 and the camera head 13 in the endoscope 10 according to the present embodiment has been described above in detail with reference to FIG. 2 to FIG. 6. While an example in which the optical element 12 is configured as the birefringent mask has been described above, as long as characteristics of the series of optical systems can be changed as described with reference to FIG. 4 to FIG. 6, the configuration is not particularly limited. Specifically, as described above, the optical element 12 may be configured as the cubic phase mask.

3. RESTORATION PROCESSING

Next, the description will proceed particularly with a focus on a configuration and a process for implementing the above-described restoration processing (image processing) as characteristics of the medical image processing system 1 according to the present embodiment.

3.1. Configuration of Image Processing Device

Figure 7:
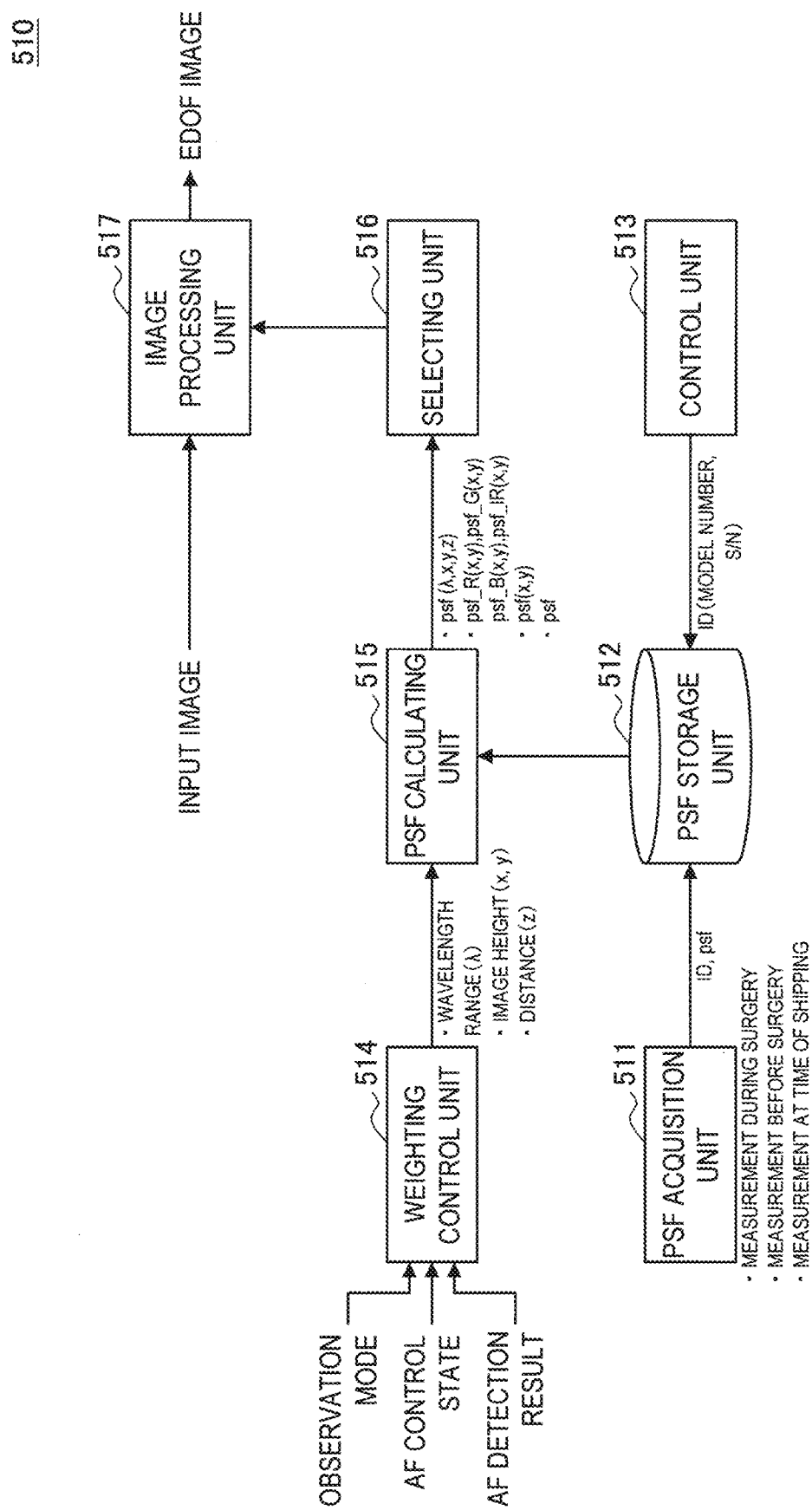
FIG. 7 is a block diagram showing an example of a functional configuration of an image processing device according to the embodiment.

First, an example of a functional configuration of a part that is particularly operated as an image processing device among various configurations of the CCU 51 shown in FIG. 1 will be described with reference to FIG. 7. FIG. 7 is a block diagram showing an example of a functional configuration of an image processing device according to the present embodiment.

As shown in FIG. 7, an image processing device 510 according to the present embodiment includes a PSF acquisition unit 511, a PSF storage unit 512, a control unit 513, a weighting control unit 514, a PSF calculating unit 515, a selecting unit 516 and an image processing unit 517.

As in the lens barrel 11 and the optical element 12 shown in FIG. 1, the PSF acquisition unit 511 acquires information indicating characteristics of the series of optical systems configured to form a subject image on the imaging element in the camera head 13 as PSF information based on a measurement result of, for example, a point spread function (psf). Examples of a trigger to acquire PSF information (that is, a trigger to measure a psf) include triggers at the time of shipping the endoscope 10, before a sample is observed (before surgery) and while a sample is observed (during surgery). A method of acquiring PSF information in each of the triggers (that is, a method of measuring a psf) will be separately described below in detail using examples.

The PSF acquisition unit 511 acquires PSF information corresponding to the instrument based on a measurement result of a psf of an instrument (for example, an optical system of the camera head 13, the lens barrel 11 connected to the camera head 13 and the optical element 12) that is used to observe the sample. In addition, in this case, the PSF acquisition unit 511 may acquire PSF information corresponding to an instrument for each condition of an observation range based on a psf of each instrument that is measured in each condition of the observation range.

Examples of the condition of the observation range include a condition of a range of, for example, an image height, a distance in the optical axis direction and a wavelength. In this description, the "image height" corresponds to a position of an optical system to be used in an image forming plane, in other words, corresponds to a position in an image that is captured using the optical system. A condition of a range of the image height may be set for directions (that is, the x direction and the y direction) that are perpendicular to each other on the image forming plane of the optical system. In addition, in this description, a "range of a distance in the optical axis direction" corresponds to a range of a distance in the optical axis direction (hereinafter referred to as the z direction) of the optical system between an optical system to be used (for example, the lens barrel 11 and the optical element 12) and a sample (a subject). In addition, in this description, "a range of a wavelength" indicates a range of a wavelength of a light component (for example, a spectral component) serving as an observation target within light that is collected by the optical system (for example, the lens barrel 11 and the optical element 12) and captured by the imaging element.

Then, the PSF acquisition unit 511 stores the acquired PSF information corresponding to each instrument in association with identification information indicating the instrument and information indicating a condition of the observation range when PSF is measured in the PSF storage unit 512. Examples of the identification information indicating each of the instruments include a model number and a serial number (S/N) of the instrument.

The PSF storage unit 512 stores the PSF information acquired by the PSF acquisition unit 511. The PSF storage unit 512 may be configured as, for example, a so-called database (DB). The PSF storage unit 512 stores PSF information corresponding to each instrument (that is, the lens barrel 11, the optical element 12 and the camera head 13) in association with information indicating the instrument and information indicating a condition for acquiring the PSF information (for example, a condition of the observation range). As a more specific example, the PSF storage unit 512 may store PSF information for each combination in which an optical characteristic is changed, for example, a combination of the lens barrel 11 and the camera head 13, installation or non-installation of the optical element 12 and a type of the optical element 12. In this case, the above-described PSF acquisition unit 511 may acquire PSF information for each combination in which an optical characteristic is changed.

In addition, the PSF storage unit 512 can selectively output the stored PSF information. As a specific example, the PSF storage unit 512 receives a notification of identification information of each instrument from the control unit 513 to be described below and outputs the PSF information associated with the identification information to the PSF calculating unit 515 to be described below.

The control unit 513 controls various operations of the medical image processing system 1 (particularly, the endoscope 10). The control unit 513 may instruct the PSF storage unit 512 to output PSF information corresponding to an instrument according to the instrument (that is, an instrument used to observe a sample) that is installed at the medical image processing system 1 such as the camera head 13, the lens barrel 11 and the optical element 12. In this case, for example, the control unit 513 recognizes each instrument such as the camera head 13, the lens barrel 11 and the optical element 12 (for example, acquires it from meta information of each instrument) and may notify the PSF storage unit 512 of identification information corresponding to the instrument based on a recognition result. Accordingly, the PSF storage unit 512 can extract PSF information to be output based on the identification information that has been notified of. As long as the control unit 513 can recognize each instrument such as the camera head 13, the lens barrel 11 and the optical element 12, a method thereof is not particularly limited. For example, the control unit 513 acquires identification information stored in each instrument from the instrument and thus may recognize the instrument.

The weighting control unit 514 and the PSF calculating unit 515 assign a weight according to a condition related to observation of a sample to PSF information that is output from the PSF storage unit 512 according to an instrument to be used and calculate PSF information according to the condition.

Specifically, the weighting control unit 514 calculates a spread function according to a condition of a range serving as a weighting target (in other words, a condition related to the observation range) according to various conditions related to observation of a sample and a weight for adjusting a value (in other words, an amount of blur) of the modulation transfer function (MTF) in the range. As described above, the condition of the observation range includes, for example, a range of a wavelength ($\lambda$) of a light component serving as an observation target, an area (x, y) in an image and the depth direction (z).

Specifically, when a weight is assigned to PSF information according to a light component (for example, a spectral component) serving as the observation target, the weighting control unit 514 calculates a spread function $Ch(\lambda)$ for adjusting an amount of blur according to the wavelength ($\lambda$) of the light component. As a specific example, when a weight is assigned to PSF information mainly using a red component (R) as a target, the weighting control unit 514 may calculate a spread function $Ch(\lambda)$ for assigning a weight to sensitivity of, for example, a red pixel (R pixel), for each wavelength. In the following description, particularly, spread functions $Ch(\lambda)$ corresponding to a red component (R), a green component (G), a blue component (B) and an infrared component (IR) may be referred to as $R(\lambda)$, $G(\lambda)$, $B(\lambda)$ and $IR(\lambda)$, respectively.

Figure 8:
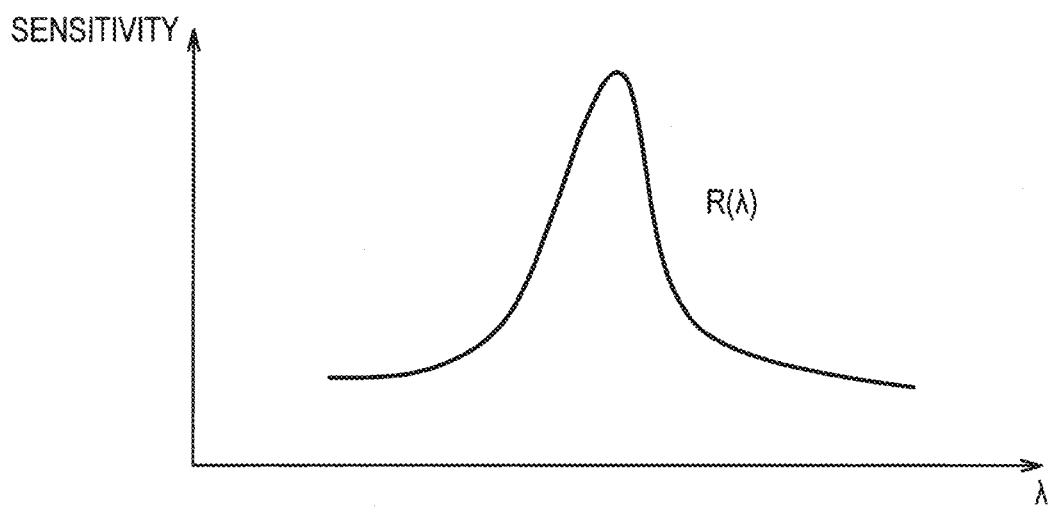
FIG. 8 is an explanatory diagram for describing an example of a spread function for assigning a weight to PSF information.

For example, FIG. 8 is an explanatory diagram for describing an example of a spread function for assigning a weight to PSF information and shows an example of a spread function $R(\lambda)$ corresponding to a red component. In FIG. 8, a horizontal axis represents a wavelength ($\lambda$) and a vertical axis represents sensitivity. The spread function $R(\lambda)$ may be calculated in consideration of not only sensitivity of the R pixel but also a characteristic of illumination light (referred to as illumination light information) and a characteristic of the optical system. In addition, while this description has focused on an example of the spread function $R(\lambda)$ corresponding to the red component, the description also applies to spread functions (that is, spread functions $G(\lambda)$, $B(\lambda)$ and $IR(\lambda)$) corresponding to other spectral components.

As long as a spread function corresponding to each spectral component can be calculated, a method of calculating the spread function is not necessarily limited to the above example. For example, even if an imaging element in which no pixel (IR pixel) corresponding to infrared light is provided is applied, for example, according to sensitivity of infrared light (IR) in an R pixel, a G pixel and a B pixel, a spread function for assigning a weight to sensitivity of the pixel for each wavelength may be calculated as a spread function $IR(\lambda)$ corresponding to the infrared component (IR).

In addition, the weighting control unit 514 calculates a spread function $a(z)$ for adjusting an amount of blur according to a position in the depth direction (that is, the z direction) when a weight is assigned to PSF information according to a position in the depth direction (that is, the optical axis direction).

Figure 9:
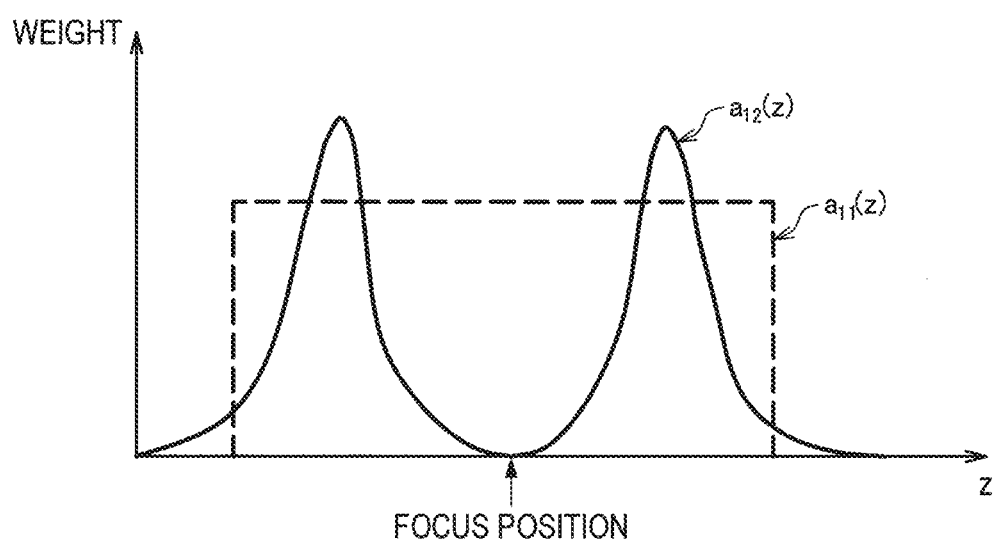
FIG. 9 is an explanatory diagram for describing an example of a spread function for assigning a weight to PSF information.

For example, FIG. 9 is an explanatory diagram for describing an example of a spread function for assigning a weight to PSF information and shows an example of a spread function $a(z)$ for assigning a weight according to a position in the depth direction. In FIG. 9, a horizontal axis represents a deviation (that is, an amount of defocus) in the optical axis direction (the z direction) using a focus position as a reference and a vertical axis represents a magnitude of a weight. In FIG. 9, a spread function $a_{11}(z)$ shows an example of a spread function when a weight is uniformly added to a value of the modulation transfer function (MTF) whose target is a predetermined range in the optical axis direction using a focus position as a reference. In addition, a spread function $a_{12}(z)$ shows an example of a spread function when a weight to be added is changed according to a position in the optical axis direction using a focus position as a reference. More specifically, the spread function $a_{12}(z)$ corresponds to a spread function that does not improve the modulation transfer function (MTF) at the focus position, but further improves the modulation transfer function (MTF) before and after the focus position. That is, when the spread function $a_{12}(z)$ is used, for example, since blur occurring before and after the focus position is reduced, it is possible to further extend a depth of field, compared to when the spread function $a_{11}(z)$ is applied.

In addition, when a weight is assigned to PSF information according to an area in an image (in other words, an image height), the weighting control unit 514 calculates a spread function $d(x, y)$ for adjusting an amount of blur according to the area in the image (that is, in the x direction and the y direction).

Figure 10:
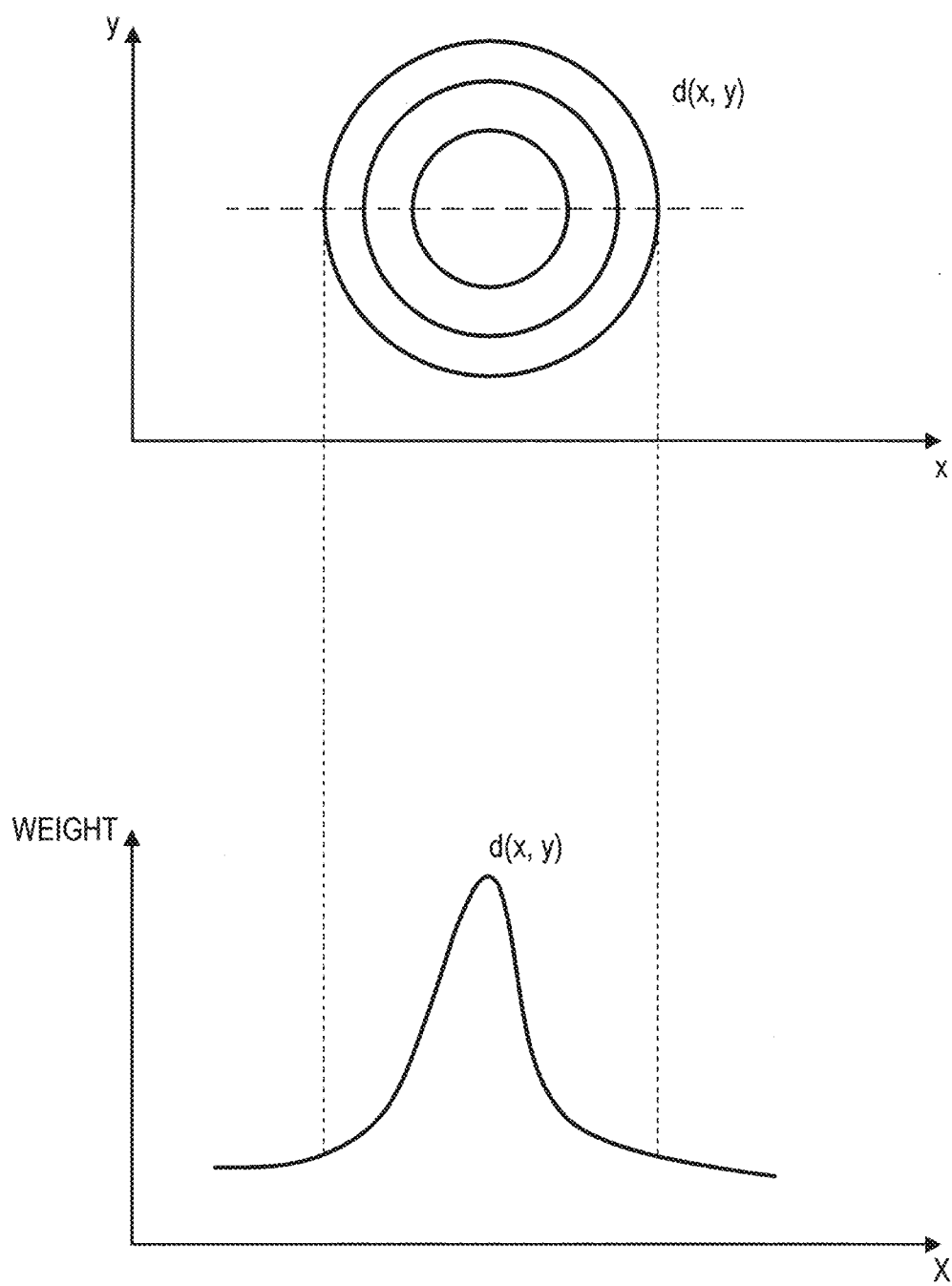
FIG. 10 is an explanatory diagram for describing an example of a spread function for assigning a weight to PSF information.

For example, FIG. 10 is an explanatory diagram for describing an example of a spread function for assigning a weight to PSF information and shows an example of a spread function $d(x, y)$ for assigning a weight to PSF information according to an area in an image. In FIG. 10, the upper graph is a graph schematically showing a distribution of a spread function $d(x, y)$ in an image, a horizontal axis represents a position (x) in the lateral direction of the image and a vertical axis represents a position (y) in the longitudinal direction of the image. In addition, the lower graph is a graph of a spread function $d(x, y)$ in a part indicated by a dashed line in the upper graph in the x direction, and a horizontal axis represents a position (x) in the lateral direction of the image and a vertical axis represents a weight, similarly to the upper graph.

In addition, examples of the condition related to observation of a sample include an observation mode that is selected according to a surgical procedure of surgery, a control state of focus point detection based on a predetermined auto focus (AF) method when a sample is imaged by the camera head 13 and a state of detection for the focus point detection.

For example, the weighting control unit 514 may decide whether it is desirable to further extend a depth of field or it is desirable to further increase a sense of resolution based on the observation mode selected according to the surgical procedure of the surgery. In this case, the weighting control unit 514 calculates a spread function $a(z)$ for assigning a weight according to a position in the depth direction to PSF information based on the decision result. In addition, as another example, the weighting control unit 514 may calculate a spread function $Ch(\lambda)$ for assigning a weight according to a wavelength of a light component to PSF information based on an observation mode selected according to an observation method such as special light observation using at least a part of a spectral component as a target. Examples of the special light observation include near-infrared fluorescence observation. In addition, in this case, the weighting control unit 514 may calculate the spread function Ch(λ) for each spectral component using a plurality of spectral components as targets. A more specific example of a relation between various conditions related to observation of a sample and the above-described various spread functions will be separately described below with reference to examples.

As described above, the weighting control unit 514 calculates a spread function according to the condition related to observation of a sample and outputs the calculated spread function to the PSF calculating unit 515.

The PSF calculating unit 515 acquires the spread function calculated according to the condition related to observation of a sample from the weighting control unit 514. In addition, the PSF calculating unit 515 acquires PSF information (hereinafter referred to as "PSF information for each instrument") according to an instrument that is used to observe a sample from the PSF storage unit 512. Then, the PSF calculating unit 515 assigns a weight based on the acquired spread function to the acquired PSF information for each instrument and calculates new PSF information according to the condition related to observation of a sample.

The PSF calculating unit 515 may calculate new PSF information for each condition (that is, for each condition of the observation range) of a range of, for example, a wavelength (λ) of a light component serving as an observation target, an area (x, y) in an image and the depth direction (z).

For example, the following (Formula 1) represents an example in which, mainly using a red component (R) as a target, a weight according to a wavelength (λ) of a light component is assigned to PSF information for each instrument and thus new PSF information according to the condition related to observation of a sample is calculated. In (Formula 1), psf(λ, x, y, z) denotes PSF information for each instrument. In addition, R(λ) denotes a spread function corresponding to the above-described red component.

[Math. 1]

$$\mathrm{psf\_}R(x,y,z)=\int_\lambda R(\lambda)[\mathrm{psf}(\lambda,x,y,z)]d\lambda \quad \text{(Formula 1)}$$

In addition, with respect to psf_R(x, y, z) shown in (Formula 1), additionally, a weight may be assigned based on a spread function according to the depth direction. For example, the following (Formula 2) represents an example in which a weight based on a spread function a(z) according to the depth direction is further assigned to the PSF information (that is, psf_R(x, y, z)) calculated based on the above (Formula 1).

[Math. 2]

$$\mathrm{psf\_}R(x,y)=\int_z a(z)[\mathrm{psf\_}R(x,y,z)]dz \quad \text{(Formula 2)}$$

While an example of calculating new PSF information by assigning a weight mainly using a red component (R) as a target based on (Formula 1) and (Formula 2) has been described above, this is similarly applied to other spectral components. That is, with respect to psf(λ, x, y, z), a weight is assigned based on a spread function G(λ) corresponding to a green component and a spread function a(z) according to the depth direction and thus it is possible to calculate psf_G(x, y) as new PSF information corresponding to a green component (G). Similarly, it is also possible to calculate psf_B(x, y) corresponding to a blue component (B) and psf_IR(x, y) corresponding to an infrared component (IR). The PSF information calculated for each spectral component in this manner (that is, psf_R(x, y, z), psf_G(x, y, z), psf_B(x, y, z) and psf_IR(x, y, z)) is used when restoration processing in response to a decrease (that is, blur) in a value of the modulation transfer function (MTF) for each spectral component is performed on an image captured by the camera head 13 by, for example, the image processing unit 517 to be described below.

In addition, according to a position (x, y) in an image in addition to the spectral component, the PSF calculating unit 515 may calculate psf(x, y) based on PSF information for performing the restoration processing for each of the above-described spectral components as PSF information for performing restoration processing in response to a decrease (that is, blur) in a value of the modulation transfer function (MTF). For example, psf(x, y) is calculated based on the following (Formula 3).

[Math. 3]

$$\mathrm{psf}(x,y)=\sum_{ch\in R,G,B,IR} w(Ch)[\mathrm{psf\_}Ch(x,y)] \quad \text{(Formula 3)}$$

In addition, in addition to a position (x, y) in an image, as PSF information when restoration processing is uniformly performed in response to a decrease (that is, blur) of a value of the modulation transfer function (MTF), the PSF calculating unit 515 may calculate a psf based on PSF information for performing the restoration processing according to the position (x, y) in the image. For example, a psf is calculated based on the following (Formula 4). In (Formula 4), d(x, y) is a spread function for assigning a weight according to the position in the image described above.

[Math. 4]

$$\mathrm{psf}=\int_{x,y}d(x,y)[\mathrm{psf}(x,y)]dxdy \quad \text{(Formula 4)}$$

As described above, the PSF calculating unit 515 assigns a weight based on a spread function according to a condition related to observation of a sample to PSF information for each instrument and thus newly calculates PSF information according to the condition. Then, the PSF calculating unit 515 outputs the calculated PSF information to the selecting unit 516. In this case, as described above, the PSF calculating unit 515 may output each piece of PSF information calculated according to the condition of the observation range based on (Formula 1) to (Formula 4) to the selecting unit 516. In addition, the PSF calculating unit 515 may output PSF information for each instrument (that is, the above-described psf(λ, x, y, z)) to which no weight is assigned to the selecting unit 516.

The selecting unit 516 acquires at least one piece of PSF information calculated according to various conditions related to observation of a sample from the PSF calculating unit 515 and selects at least a part of PSF information from among the acquired at least one piece of PSF information based on a predetermined condition.

For example, the selecting unit 516 may select PSF information through which it is possible to observe the sample in a more suitable manner based on a type of special light observation and an observation mode selected according to a surgical procedure of surgery. More specifically, the selecting unit 516 may select PSF information so that restoration processing is performed on a specific spectral component according to a type of special light observation. In addition, as another example, the selecting unit 516 may select PSF information for further increasing a depth of field according to a surgical procedure of surgery and may select PSF information for acquiring an image in which a sharper sample is presented (that is, an image having a high sense of resolution). In addition, since a surgical procedure may differ according to a diagnosis and treatment department in which the medical image processing system 1 is used, for example, the selecting unit 516 may select PSF information according to information indicating the diagnosis and treatment department. It should be noted that the selecting unit 516 may receive explicit designation from the user and select the designated PSF information.

In addition, the selecting unit 516 may adaptively switch PSF information according to a state and situation related to observation of a sample. As a specific example, the selecting unit 516 may select PSF information according to a kind, a shape and a color of a subject (a sample or an affected part) based on an analysis result of the captured image. In this case, as a configuration of the image processing device 510, a configuration for performing analysis processing on the captured image may be provided.

In addition, when the medical image processing system 1 according to the present embodiment is configured as an observation system capable of observing a stereoimage of a subject, the selecting unit 516 may select PSF information according to, for example, a change in a parallax value between images corresponding to different points of view (that is, a right eye and a left eye). In this case, for example, a configuration for capturing an image corresponding to each of the points of view (that is, an optical system in the lens barrel 11 and an imaging element in the camera head 13) may be provided. In addition, as a configuration of the image processing device 510, a configuration for calculating a parallax value between the captured images corresponding to the points of view may be provided.

Then, the selecting unit 516 outputs the selected PSF information to the image processing unit 517.

The image processing unit 517 acquires PSF information from the selecting unit 516, uses the image captured by the camera head 13 as an input image, performs restoration processing based on the PSF information acquired for the input image, and reduces deterioration (that is, blur) in a subject image. Examples of the restoration processing include processing that is so-called deconvolution. As a more specific example, the image processing unit 517 performs image processing (for example, filter processing) based on an inverse characteristic of the PSF information acquired from the input image and reduces deterioration (blur) in the image that occurs according to an optical characteristic indicated by the PSF information. It should be noted that, as long as it is possible to reduce deterioration of the subject image based on PSF information, restoration processing that is performed on the input image is not necessarily limited to the deconvolution. The image on which restoration processing is performed by the image processing unit 517 is presented to the user through, for example, the display device 53 shown in FIG. 1.

In such a configuration, in the image processing device 510 according to the present embodiment, according to the condition related to observation of a sample such as an observation environment, an observation target and an observation method, it is possible to acquire an image in which it is possible to observe the sample in a more suitable manner. More specifically, for example, it is possible to reduce deterioration of the modulation transfer function (MTF) caused by insertion of the optical element 12 that has been described with reference to FIG. 4 to FIG. 6 and it is possible to acquire an extended depth of field (EDOF) image in which a depth of field is further extended. In addition, it is possible to acquire an image in which deterioration of the subject image is reduced even when special light observation is performed, according to a spectral component serving as the observation target.

However, the functional configuration shown in FIG. 7 is only an example. As long as it is possible to implement operations of configurations of the above-described image processing device 510, the functional configuration of the image processing device 510 is not necessarily limited to the example shown in FIG. 7. As a specific example, some of the configurations of the above-described image processing device 510 may be provided outside the image processing device 510. As a more specific example, the PSF acquisition unit 511 and the PSF storage unit 512 may be provided in an external device (for example, a server) that is connected to the image processing device 510 via network. In addition, the image processing device 510 may be provided in, for example, the endoscope 10 described with reference to FIG. 1.

An example of a functional configuration of a part that is particularly operated as the image processing device within the configuration of the CCU 51 shown in FIG. 1 has been described above with reference to FIG. 7 to FIG. 10.

3.2. Process of Image Processing Device

Figure 11:
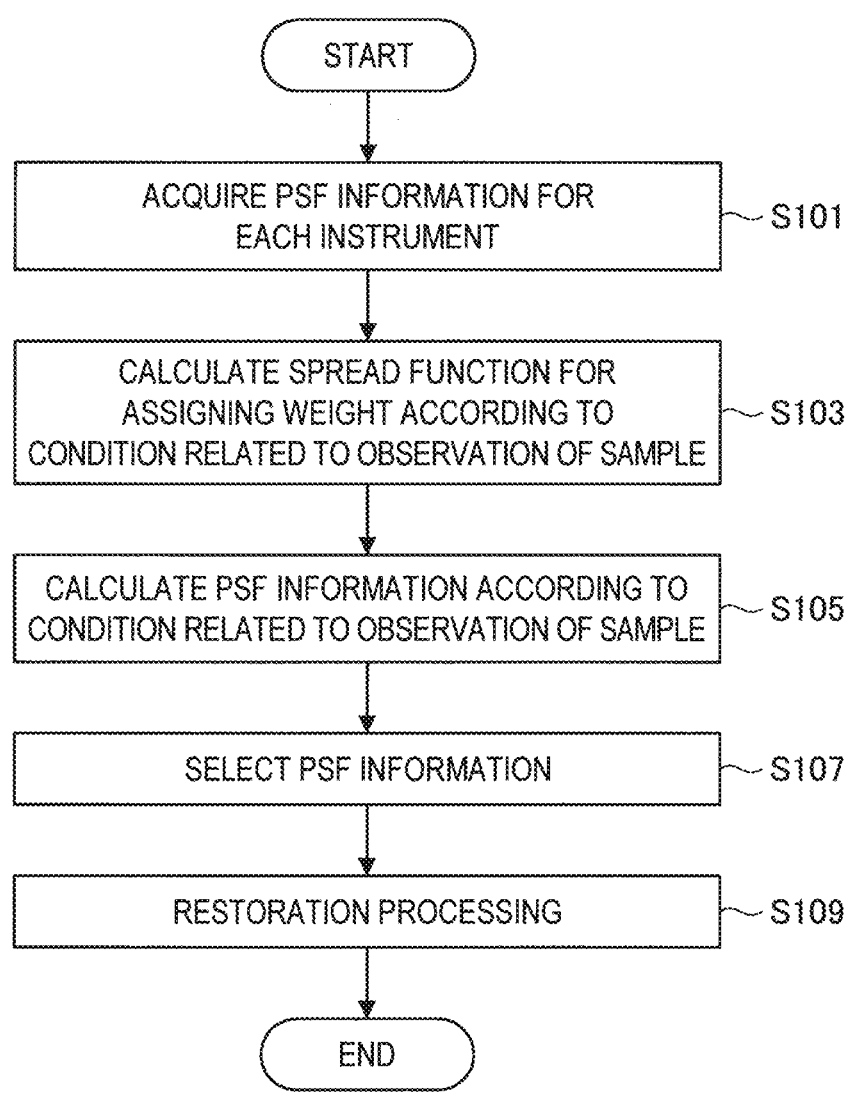
FIG. 11 is a flowchart showing an example of a flow of a series of processes of an image processing device according to the embodiment.

Next, an example of a flow of a series of processes of the image processing device 510 according to the present embodiment will be described with reference to FIG. 11. FIG. 11 is a flowchart showing an example of a flow of a series of processes of the image processing device 510 according to the present embodiment.

As shown in FIG. 11, the image processing device 510 (the PSF acquisition unit 511) acquires PSF information corresponding to an instrument based on a measurement result of a psf for each instrument that is used to observe a sample. In this case, the image processing device 510 may acquire PSF information corresponding to the instrument for each condition of the observation range based on a psf of the instrument measured for each condition related to observation. Then, the image processing device 510 stores the acquired PSF information corresponding to each instrument in association with identification information indicating the instrument and information indicating a condition related to observation when PSF is measured (S101).

Next, the image processing device 510 (the weighting control unit 514) calculates a spread function according to a condition of a range serving as a weighting target according to the condition related to observation of a sample and a weight for adjusting a value (in other words, an amount of blur) of the modulation transfer function (MTF) in the range (S103). Since the method of calculating a spread function according to the condition has been described above as the operation of the weighting control unit 514, details thereof will be omitted.

Next, the image processing device 510 (the PSF calculating unit 515) assigns a weight based on a spread function calculated according to a condition related to observation of a sample to PSF information corresponding to an instrument that is used to observe a sample and thus calculates new PSF information according to the condition (S105). In this case, the image processing device 510 may calculate new PSF information for each condition (that is, the condition of the observation range) of a range of, for example, a wavelength (λ) of a light component serving as an observation target, an area (x, y) in an image and the depth direction (z). Since the method of calculating PSF information according to the condition has been described above as the operation of the PSF calculating unit 515, details thereof will be omitted.

Next, the image processing device 510 (the selecting unit 516) selects at least a part of PSF information from among at least one piece of PSF information calculated according to various conditions related to observation of a sample based on a predetermined condition (S107). For example, the image processing device 510 may select PSF information according to the selected observation mode. In addition, as another example, the image processing device 510 may receive explicit designation from the user and select the designated PSF information. In addition, as another example, the image processing device 510 may adaptively switch PSF information according to a state and situation related to observation of a sample.

Then, the image processing device 510 (the image processing unit 517) uses the image captured by the camera head 13 as an input image, performs restoration processing such as deconvolution on deterioration (that is, blur) of the subject image based on PSF information selected for the input image, and thus restores the image (S109). The image on which restoration processing is performed by the image processing unit 517 is presented to the user through, for example, a predetermined display device.

The example of a flow of a series of processes of the image processing device 510 according to the present embodiment has been described above with reference to FIG. 11.

4. EXAMPLES

Next, examples of the present embodiment will be described.

4.1. Example 1: Acquisition of PSF Information for Each Instrument

First, as Example 1, an example of a method of acquiring PSF information corresponding to an instrument by measuring a psf for each instrument that is used to observe a sample will be described.

Example 1-1: Acquisition Method Before Shipping

Figure 12:
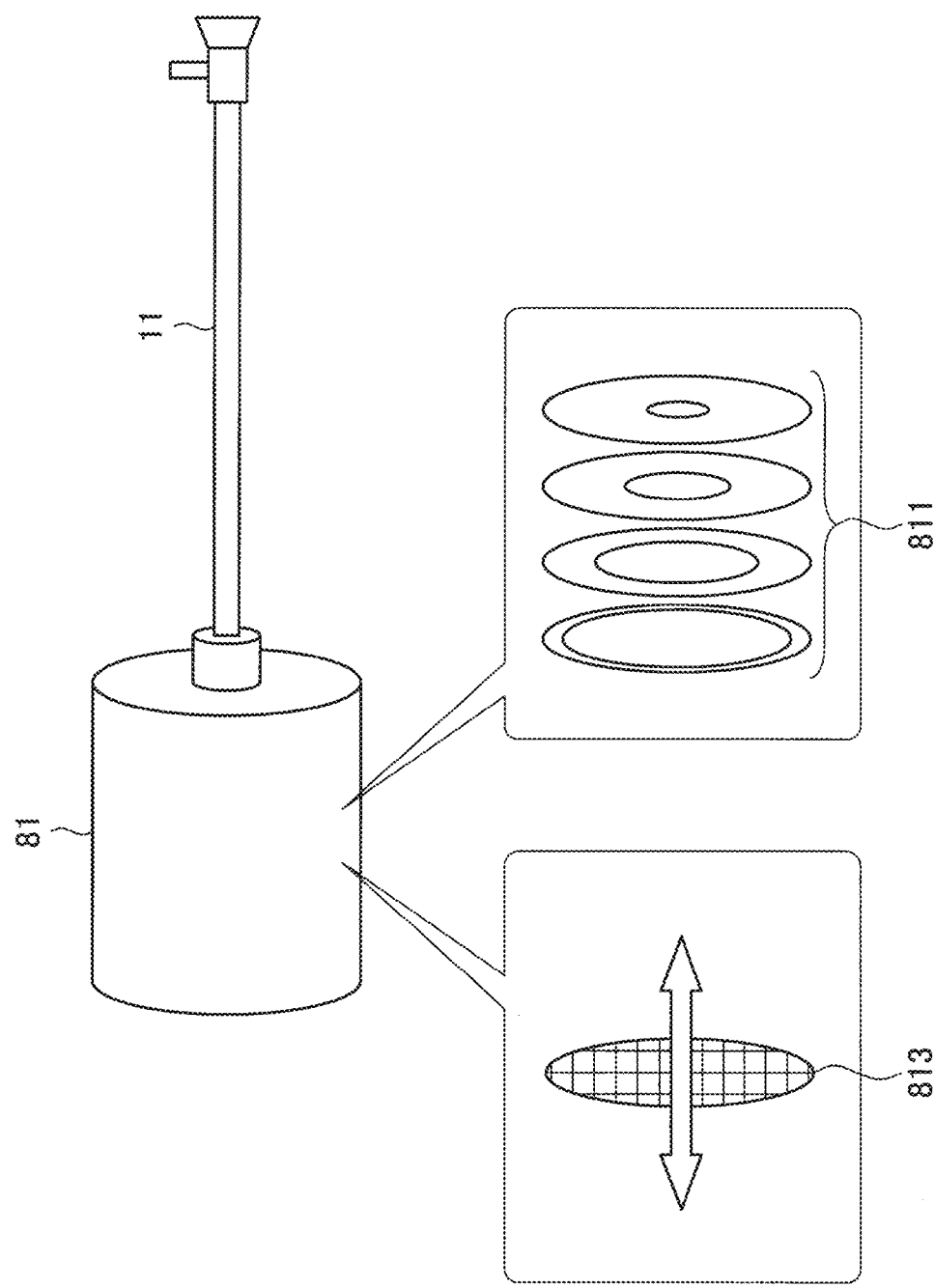
FIG. 12 is an explanatory diagram for describing an example of a method of acquiring PSF information in an endoscopic device according to Example 1-1.

First, as Example 1-1, examples of a configuration and a method of acquiring PSF information corresponding to an instrument before shipping a series of instruments such as the lens barrel 11, the optical element 12 and the camera head 13 shown in FIG. 1 will be described with reference to FIG. 12. FIG. 12 is an explanatory diagram for describing an example of a method of acquiring PSF information in an endoscopic device according to Example 1-1 of the present embodiment.

In the example shown in FIG. 12, a measurement fixture 81 is installed at the distal end of the lens barrel 11, an image in the measurement fixture 81 is captured through the lens barrel 11 and thus a psf of the lens barrel 11 is measured.

In the measurement fixture 81, for example, a plurality of transparent disks on which circles are drawn as indicated by a reference sign 811 are mounted on the lens barrel 11 that is installed at the measurement fixture 81 in the optical axis direction (that is, the z direction). In this case, for example, circles having different radii are drawn on the plurality of disks. In such a configuration, when an inside of the measurement fixture 81 is imaged through the lens barrel 11, the circles drawn on the disks are imaged without overlapping. In such a configuration, it is possible to measure a psf according to a position in the depth direction (the z direction) according to an amount of blur of circles of the disks in the captured image.

In the example indicated by the reference sign 811, an example in which one circle is drawn on each disk is shown, but a plurality of circles having different radii may be concentrically drawn on each disk. In such a configuration, for example, it is possible to measure psf(x, y, z) according to a position (that is, a position on the xy plane) in the captured image for each position in the depth direction (that is, the z direction). In addition, when an image of the inside of the measurement fixture 81 is captured while a wavelength λ of illumination light is changed, it is possible to measure psf(λ, x, y, z) for each wavelength λ of the light component based on the image captured for each wavelength λ.

In addition, as indicated by a reference sign 813, in the measurement fixture 81, a disk on which a grid is drawn is provided to be movable in the optical axis direction (that is, the z direction) of the lens barrel 11 that is installed at the measurement fixture 81. A configuration of moving the disk in the optical axis direction is not particularly limited. For example, a configuration in which the disk can be manually moved or a configuration in which the disk can be moved according to electricity generated by driving a driving unit such as a motor may be used. In such a configuration as well, the disk on which a grid is drawn is moved in the z direction and an image of the inside of the measurement fixture 81 is captured for each position in the z direction. Therefore, it is possible to measure psf(x, y, z) according to the position in the captured image for each position in the depth direction (the z direction) according to an amount of blur of the grid in each position (that is, a position on the xy plane) in the captured image.

In addition, in the example indicated by the reference sign 813 as well, when an image of the inside of the measurement fixture 81 is captured while a wavelength λ of illumination light is changed, it is possible to measure psf(λ, x, y, z) for each wavelength λ of a light component based on the captured image for each wavelength λ.

In addition, for example, when the optical element 12 and the camera head 13 are installed at the lens barrel 11 as described above and an image of the inside of the measurement fixture 81 is captured, it is possible to measure a psf of a series of instruments of the lens barrel 11, the optical element 12 and the camera head 13 based on the captured image.

The PSF information based on a psf measured as described above may be stored in, for example, the PSF storage unit 512 described with reference to FIG. 7.

The examples of the configuration and the method of acquiring PSF information corresponding to an instrument before shipping a series of instruments such as the lens barrel 11, the optical element 12 and the camera head 13 shown in FIG. 1 have been described above with reference to FIG. 12.

Example 1-2: Acquisition Method Before Surgery

Figure 13:
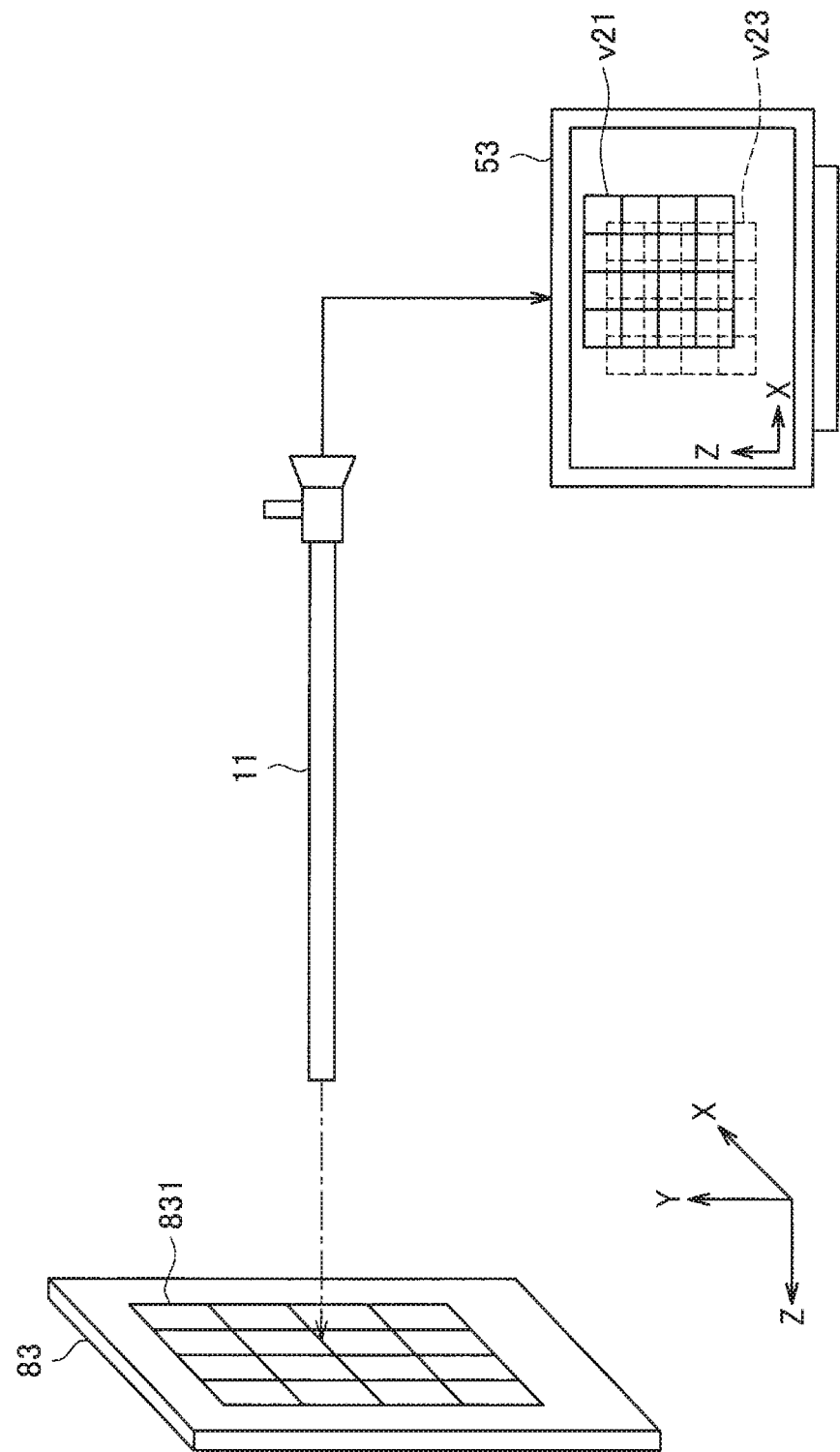
FIG. 13 is an explanatory diagram for describing an example of a method of acquiring PSF information in an endoscopic device according to Example 1-2.
Figure 14:
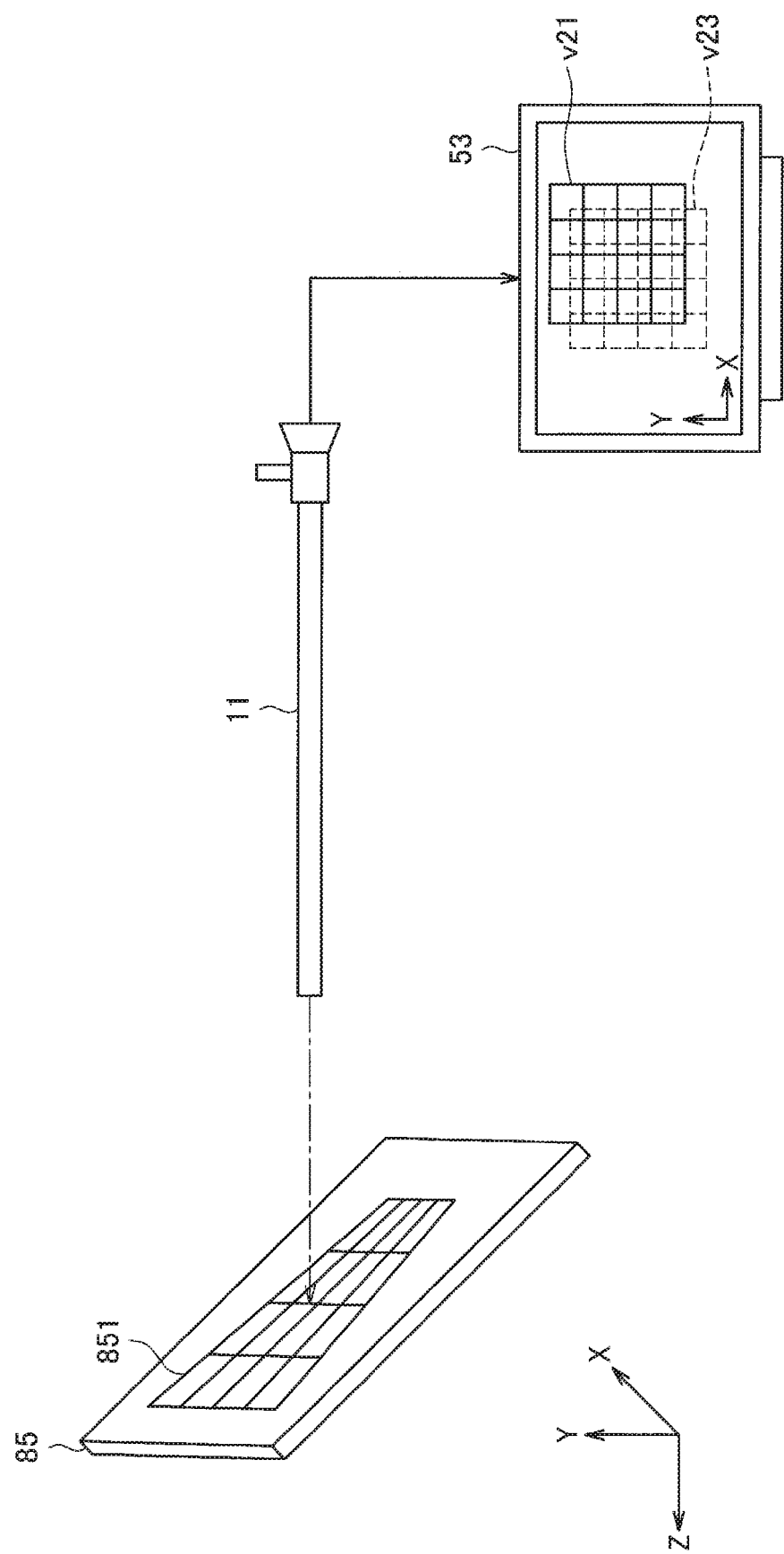
FIG. 14 is an explanatory diagram for describing an example of a method of acquiring PSF information in an endoscopic device according to Example 1-2.

Next, as Example 1-2, examples of a configuration and a method of acquiring PSF information by measuring a psf of an instrument in a more simplified manner in a situation in which it is difficult to allocate a time for psf measurement itself compared to the example shown in FIG. 12, for example, before surgery, will be described with reference to FIG. 13 and FIG. 14. FIG. 13 and FIG. 14 are explanatory diagrams for describing an example of a method of acquiring PSF information in an endoscopic device according to Example 1-2 of the present embodiment.

For example, in the example shown in FIG. 13, an image of a plate 83 on which an orthogonal grid 831 is drawn is captured by the imaging unit (for example, the camera head) through the lens barrel 11, and the captured image (a so-called preview image) is displayed on the display device 53. Accordingly, the image v21 of the grid 831 is displayed on a screen of the display device 53. In addition, on the screen of the display device 53, the adjustment guide v23 that substantially matches the image v21 of the grid 831 when the plate 83 and the lens barrel 11 have a predetermined positional relation is displayed to have a predetermined position within the screen to overlap an image that is displayed on the screen. Then, when a position of the plate 83 or the lens barrel 11 is adjusted and then the image v21 of the grid 831 matches the adjustment guide v23, an image of the grid 831 is captured by the imaging unit through the lens barrel 11. According to the above-described configuration and procedure, the image of the grid 831 when the lens barrel 11 and the grid 831 have a predetermined positional relation is acquired, and it is possible to measure psf(x, y) according to a position in the captured image according to an amount of blur of the grid 831 in each position (that is, a position on the xy plane) in the image. It is needless to say that a distance between the lens barrel 11 and the plate 83 (that is, the grid 831) in the depth direction (that is, the z direction) is uniquely decided according to a magnitude of the adjustment guide v23 if a size of the grid 831 is known.

In addition, according to the adjustment guide v23 displayed on the screen, a distance between the lens barrel 11 and the plate 83 in the depth direction for the image v21 of the grid 831 to substantially match the adjustment guide v23 differs. Therefore, when such a characteristic is used, it is possible to measure psf(x, y, z) according to a position in the depth direction (the z direction). Specifically, a display size of the adjustment guide v23 is appropriately changed and while the image v21 of the grid 831 matches the adjustment guide v23, an image of the grid 831 is captured by the imaging unit through the lens barrel 11 each time. Accordingly, based on the display size of the adjustment guide v23 and an amount of blur of the grid 831 in the captured image, it is possible to measure psf(x, y, z) according to a position in the depth direction. Also, when an optical zoom is used, psf(x, y, z) is changed according to the lens position and the magnification. Therefore, in this case, the camera head 13 acquires information (for example, a lens position and a magnification) about the optical zoom from the control unit 513 and calculates psf(x, y, z) based on the information.

In addition, similarly to the example described with reference to FIG. 12, when a wavelength λ of illumination light is changed and an image of the plate 83 is captured, it is possible to measure psf(k, x, y, z) for each wavelength λ of a light component based on the captured image for each wavelength λ.

Next, the description will focus on FIG. 14. In the example shown in FIG. 14, a grid 851 to which distortion is added and that is seen as an orthogonal grid when a plate 85 is viewed at a predetermined angle is drawn on the plate 85. That is, at a predetermined angle with respect to the plate 85, an image of the plate 85 is captured by the imaging unit through the lens barrel 11, and the captured image (a so-called preview image) is displayed on the display device 53. Therefore, the image v21 of the orthogonal grid is displayed on the screen of the display device 53. In the example shown in FIG. 14, such a characteristic is used and, similarly to the example shown in FIG. 13, the captured image v21 of the grid 851 (that is, the orthogonal grid) matches the adjustment guide v23, and then an image of the grid 851 may be captured by the imaging unit. Accordingly, it is possible to measure a psf based on an amount of blur of the grid 851 in the captured image. In this case, in the captured image of the grid 851, according to a position (that is, a position on the xy plane) in the image, a position in the depth direction (that is, the z direction) in a real space of the grid 851 differs. Therefore, in the example shown in FIG. 14, it is also possible to measure a psf at a position (a position in the depth direction) before and after the focus position by single imaging.

In the example shown in FIG. 14 as well, similarly to the example shown in FIG. 13, psf(x, y, z) according to a position in the depth direction (the z direction) may be measured. Specifically, the display size of the adjustment guide v23 is appropriately changed, and while the image v21 of the grid 851 matches the adjustment guide v23, an image of the grid 851 may be captured by the imaging unit through the lens barrel 11 each time. Accordingly, it is possible to measure psf(x, y, z) according to a position in the depth direction based on the display size of the adjustment guide v23 and an amount of blur of the grid 851 in the captured image. In addition, when a wavelength λ of illumination light is changed and an image of the plate 83 is captured, it is possible to measure psf(λ, x, y, z) for each wavelength λ of a light component based on the image captured for each wavelength λ.

The examples of the configuration and the method of acquiring the PSF information by measuring a psf of an instrument in a more simplified manner in a situation in which it is difficult to allocate a time for psf measurement itself compared to the example shown in FIG. 12, for example, before surgery, have been described above with reference to FIG. 13 and FIG. 14. While cases before shipping and before surgery are separately described in this description, it should be noted that a method is not limited to the cases before shipping and before surgery, and any method may be used at any time other than during surgery.

Example 1-3: Acquisition Method During Surgery

Figure 15:
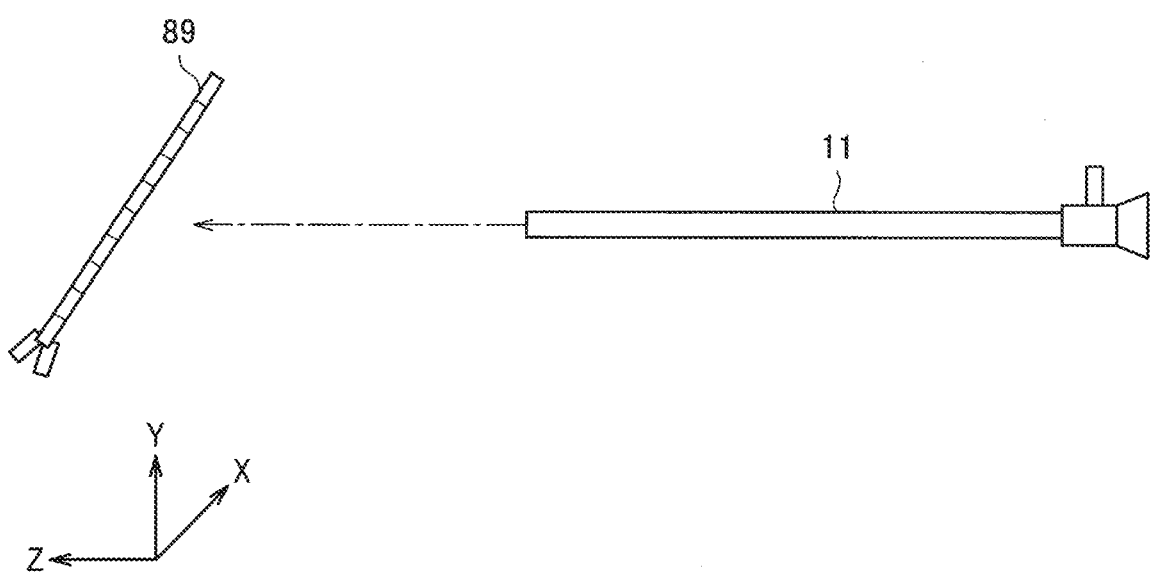
FIG. 15 is an explanatory diagram for describing an example of a method of acquiring PSF information in an endoscopic device according to Example 1-3.

Next, as Example 1-3, examples of a configuration and a method of acquiring PSF information by measuring a psf during surgery will be described with reference to FIG. 15. FIG. 15 is an explanatory diagram for describing an example of a method of acquiring PSF information in an endoscopic device according to Example 1-3 of the present embodiment.

In Example 1-3, for example, an image of a fixture such as a forceps is captured during surgery and a psf is measured based on the captured image. As a more specific example, in the example shown in FIG. 15, a forceps 87 on which a grid is drawn is used and an image of the forceps 87 is captured by the camera head 13 through the lens barrel 11. A size of the grid drawn on the forceps 87 in the image is changed according to a distance between the forceps 87 and the lens barrel 11 in the depth direction (that is, the z direction). Therefore, a psf is measured based on an amount of blur in the grid in the captured image, and a distance between the forceps 87 and the lens barrel 11 in the depth direction (that is, the z direction) is inversely calculated from the size of the grid in the image. Therefore, it is possible to measure psf(z) according to a position in the depth direction (the z direction).

As long as it is possible to calculate a distance between the forceps 87 and the lens barrel 11 in the depth direction (that is, the z direction), a capturing target of an image for measuring a psf is not necessarily limited to the forceps 87 on which the grid is drawn as the example shown in FIG. 15. For example, an image of a part whose size is known among parts of the forceps is captured and a distance between the forceps 87 and the lens barrel 11 in the depth direction (that is, the z direction) may be calculated based on an interval between edges of a part of the forceps in the image. In addition, in this case, a psf may be measured according to an amount of blur at the edge of the part of the forceps in the captured image.

The examples of the configuration and the method of acquiring PSF information by measuring a psf during surgery have been described above with reference to FIG. 15 as Example 1-3.

4.2. Example 2: Example of Calculating PSF Information According to Various Conditions Next, as Example 2, an example of control related to calculating PSF information according to a condition such as calculating a spread function according to a condition related to observation of a sample and assigning a weight to PSF information according to the spread function will be described in connection with an example of a specific scene.

Example 2-1: Control According to Fineness of Subject

First, as Example 2-1, an example of a spread function for assigning a weight to PSF information according to fineness of a subject at a focus position will be described with reference to FIG. 16. FIG. 16 is an explanatory diagram for describing an example of control related to calculating PSF information in an image processing device according to Example 2-1. In the following description, a detection value for focus point detection based on a predetermined auto focus (AF) method will be referred to as an "AF detection value." The focus point detection is performed based on, for example, contrast information, luminance information and edge information in an image.

In FIG. 16, two upper drawings show an example in which an AF detection value at a focus position is relatively large, in other words, correspond to an example in which a difference of the AF detection values between the focus position and the surroundings of the focus position is relatively large. On the other hand, two lower drawings show an example in which an AF detection value at a focus position is relatively small, in other words, correspond to an example in which a difference of the AF detection values between a focus position and the surroundings of the focus position is relatively small.

More specifically, the upper left drawing is a diagram schematically showing a distribution of the AF detection value in the image when the AF detection value at the focus position is relatively large, and numeric values shown in the drawing indicate AF detection values in areas in the image. As the numeric value shown in the drawing increases, the detection value increases, and a sharper image of the subject is captured. In this case, it can be understood that, since the AF detection value at the focus position is relatively larger than that of the surroundings of the focus position, a finer image of the subject is captured. In such a case, the image processing device 510 may calculate a spread function a(z) for assigning a weight according to a position in the depth direction (the z direction) to PSF information, for example, in order for the subject at the focus position to be presented more sharply. For example, a spread function $a_{21}(z)$ shown in the upper right drawing shows an example of a spread function a(z) that is calculated such that an integration range becomes smaller in order for the subject at the focus position to be presented more sharply. While the description has focused on the depth direction (the z direction), a desired spread function may be calculated such that, for example, a wavelength ($\lambda$) and an integration range of an area in the image (that is, in the x direction and the y direction) become smaller.

In addition, the lower left drawing is a diagram schematically showing a distribution of the AF detection value in the image when the AF detection value at the focus position is relatively small and numeric values shown in the drawing indicate AF detection values in areas in the image. In this case, it can be understood that, since a difference of the AF detection values between the focus position and the surroundings of the focus position is relatively small, a coarser subject is captured than in the upper example. In such a case, the image processing device 510 may calculate a spread function a(z) for assigning a weight according to a position in the depth direction (the z direction) to PSF information such that, for example, a depth of field is further increased. For example, a spread function $a_{22}(z)$ shown in the lower right drawing shows an example of a spread function a(z) that is calculated such that an integration range becomes larger in order to further increase a depth of field. While the description has focused on the depth direction (the z direction), a desired spread function may be calculated such that, for example, a wavelength ($\lambda$) and an integration range of an area in the image (that is, in the x direction and the y direction) become larger.

According to the control described above, it is possible to perform restoration processing on the image so that a subject can be observed in a more suitable manner according to fineness of the subject that is captured in the image. However, the above-described example is only an example. It should be noted that, as long as it is possible to control an amount of blur according to fineness of the subject that is captured in the image, content of the processing is not necessarily limited to the above example.

The example of the spread function for assigning a weight to PSF information according to fineness of the subject at the focus position has been described above with reference to FIG. 16 as Example 2-1.

Example 2-2: Control According to Degree of Focus

Figure 17:
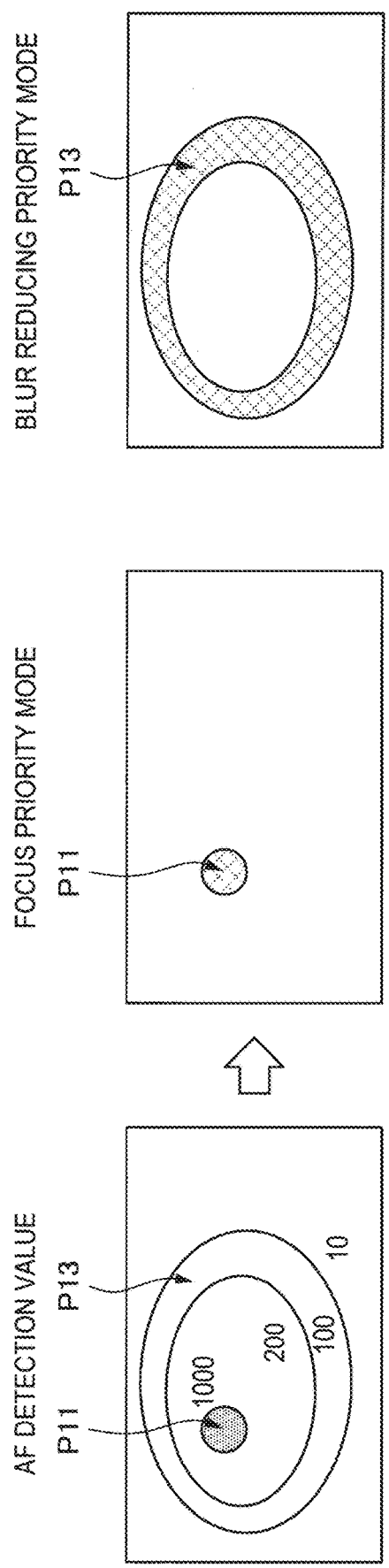
FIG. 17 is an explanatory diagram for describing an example of control related to calculating PSF information in an image processing device according to Example 2-2.
Figure 18:
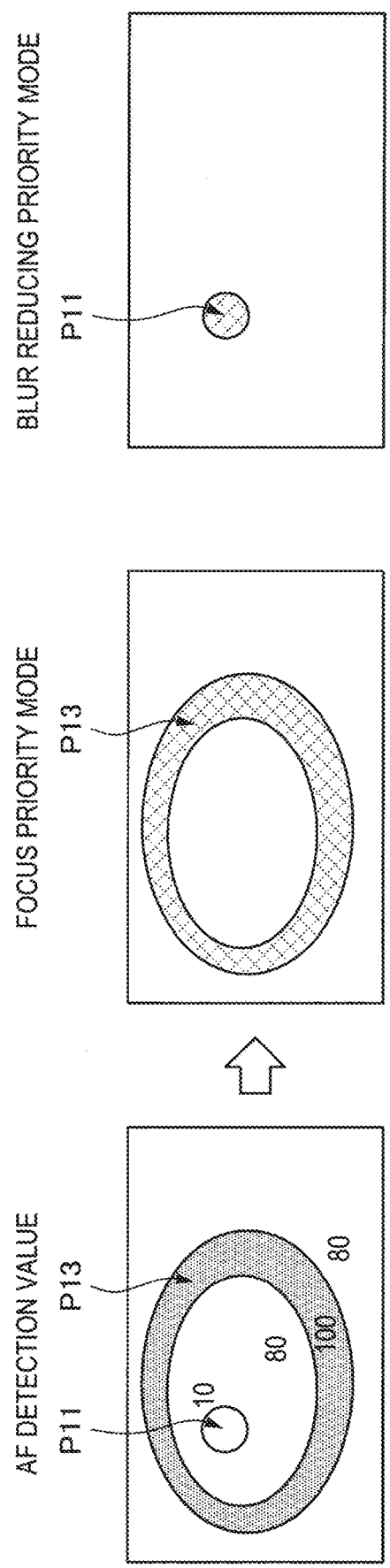
FIG. 18 is an explanatory diagram for describing an example of control related to calculating PSF information in an image processing device according to Example 2-2.

Next, as Example 2-2, an example of a method of calculating a spread function according to a degree of focus in positions in the image will be described with reference to FIG. 17 and FIG. 18. FIG. 17 and FIG. 18 are explanatory diagrams for describing an example of control related to calculating PSF information in an image processing device according to Example 2-2.

First, the description will focus on FIG. 17. Among drawings shown in FIG. 17, the left drawing is a diagram schematically showing a distribution of the AF detection value in the image and numeric values shown in the drawing indicate AF detection values in areas in the image. That is, in the example shown in FIG. 17, between areas indicated by reference signs P11 and P13, the area P11 has the highest AF detection value and the area P11 corresponds to the focus position.

In addition, among the drawings shown in FIG. 17, the center drawing is a diagram schematically showing a spread function d(x, y) for assigning a weight according to an area in an image when the image in which a subject at a focus position is presented more sharply is acquired. In the following description, a mode for acquiring the image in which a subject at a focus position is presented more sharply is referred to as a "focus priority mode." In addition, the right drawing is a diagram schematically showing a spread function d(x, y) for assigning a weight according to an area in the image when blur of the surroundings of the focus position is reduced and thus an image in which a depth of field further increases is acquired. In the following description, a mode for acquiring an image in which blur of the surroundings of the focus position is reduced and thus a depth of field further increases may be referred to as a "blur reducing priority mode."

In the example shown in FIG. 17, when the image processing device 510 is operated in the focus priority mode, for example, as shown in the center drawing, the spread function d(x, y) may be calculated such that a weight at the area P11 corresponding to the focus position further increases. In addition, when the image processing device 510 is operated in the blur reducing priority mode, for example, as shown in the right drawing, the spread function d(x, y) may be calculated such that a weight at the area P13 of the surroundings of the focus position further increases.

Next, the description will focus on FIG. 18. Among drawings shown in FIG. 18, the left drawing is a diagram schematically showing a distribution of the AF detection value in the image and numeric values shown in the drawing indicate AF detection values in areas in the image. That is, in the example shown in FIG. 18, between areas indicated by reference signs P11 and P13, the area P13 has the highest AF detection value and the area P13 corresponds to the focus position. In addition, the center drawing is a diagram schematically showing a spread function d(x, y) for assigning a weight according to an area in the image when the image processing device 510 is operated in the focus priority mode. In addition, the right drawing is a diagram schematically showing a spread function d(x, y) for assigning a weight according to an area in the image when the image processing device 510 is operated in the blur reducing priority mode.

In the example shown in FIG. 18, when the image processing device 510 is operated in the focus priority mode, for example, as shown in the center drawing, the spread function d(x, y) may be calculated such that a weight at the area P13 corresponding to the focus position further increases. In addition, when the image processing device 510 is operated in the blur reducing priority mode, for example, as shown in the right drawing, the spread function d(x, y) may be calculated such that a weight at the area P11 of the surroundings of the focus position further increases.

According to the control described above, it is possible to perform desired restoration processing on the image according to a target (that is, a target in which a focus point matches) to which an observer (the user) pays more attention among subjects that are captured in the image. However, the above-described example is only an example. It should be noted that as long as it is possible to control an amount of blur according to a degree of focus at positions in the image, content of the processing is not necessarily limited to the above example. In addition, as long as the control can be implemented, a method thereof is not limited. For example, the spread function d(x, y) may be calculated according to at least any of focus position information according to a situation of a focus in the image, focus distance information indicating a distance of a focus position in the optical axis direction and focus lens position information.

The example of the method of calculating a spread function according to a degree of focus at the positions in the image has been described above with reference to FIG. 17 and FIG. 18 as Example 2-2.

Example 2-3: Control for Each Color

Figure 19:
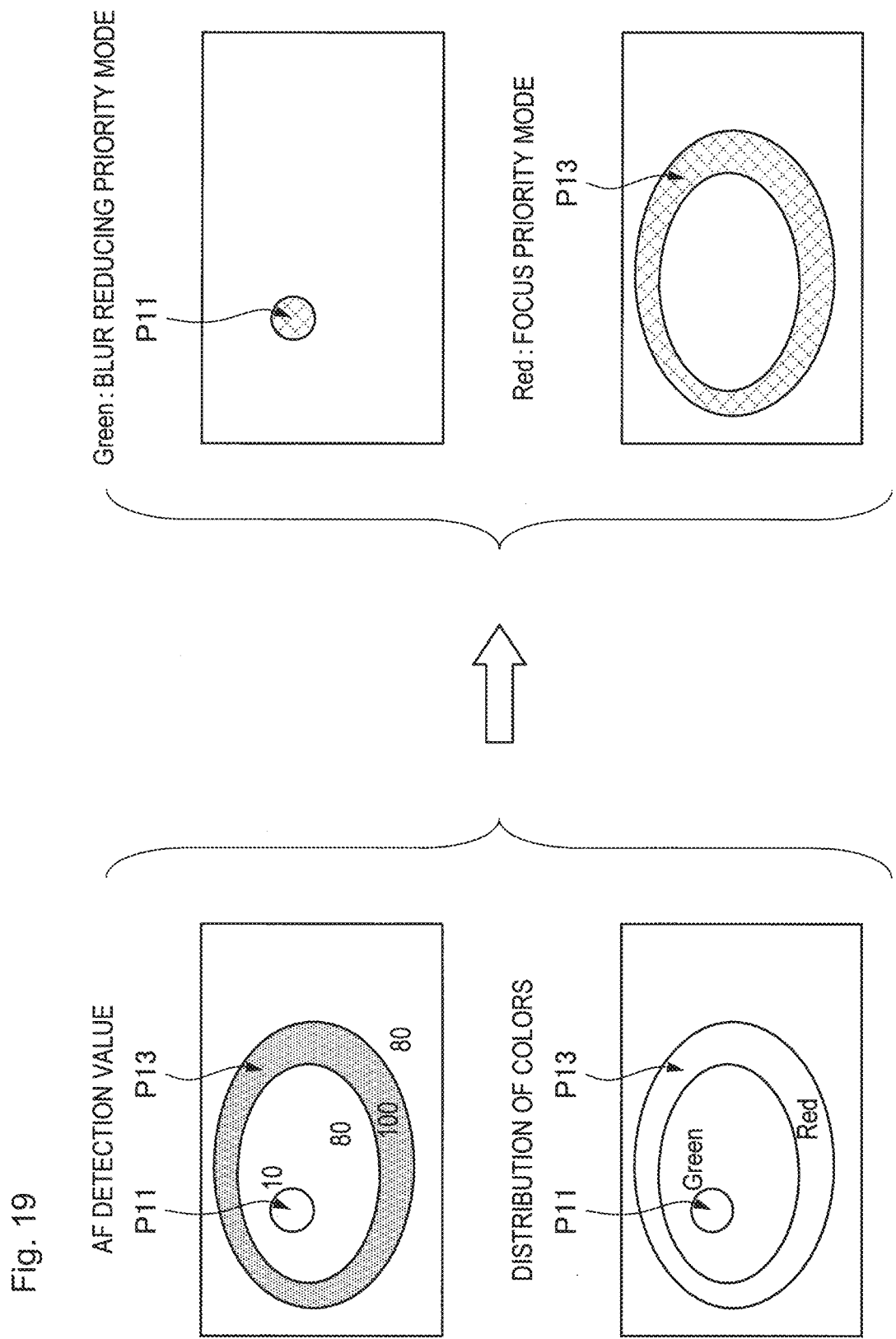
FIG. 19 is an explanatory diagram for describing an example of control related to calculating PSF information in an image processing device according to Example 2-3.

Next, as Example 2-3, an example of calculating a spread function according to a color of a subject will be described with reference to FIG. 19. FIG. 19 is an explanatory diagram for describing an example of control related to calculating PSF information in an image processing device according to Example 2-3.

Among drawings in FIG. 19, the upper left drawing is a diagram schematically showing a distribution of the AF detection value in the image, and numeric values shown in the drawing indicate AF detection values in areas in the image. In the example shown in FIG. 19, between areas indicated by reference signs P11 and P13, the area P13 has the highest AF detection value and the area P13 corresponds to the focus position. In addition, the lower left drawing is a diagram schematically showing the distribution of colors in the image. That is, in the example shown in FIG. 19, green is mainly distributed in the area P11 and red is mainly distributed in the area P13.

In addition, among the drawings shown in FIG. 19, the upper right drawing schematically shows a spread function for assigning a weight according to an area in the image mainly using a green component (G) as a target. In addition, the lower right drawing schematically shows a spread function for assigning a weight according to an area in the image mainly using a red component (R) as a target.

That is, in the example shown in FIG. 19, the image processing device 510 controls a weight of the area P11 to further increase based on, for example, the blur reducing priority mode, in a spread function $G(\lambda)$ in which a green component (G) is mainly used as a target and thus controls blur to be reduced and a depth of field to further increase. On the other hand, the image processing device 510 controls a weight of the area P13 to further increase based on, for example, the focus priority mode, in a spread function $R(\lambda)$ in which a red component (R) is mainly used as a target and thus controls a red subject (sample) to be presented more sharply.

According to the control described above, for example, it is possible to perform restoration processing on an image such that a subject of a predetermined color is emphasized more among subjects that are captured in the image. Particularly, in a situation in which an image of an inside of a living body (a so-called endoscope image) is acquired by the medical image processing system 1 according to the present embodiment, an image in which a red component is broadly distributed tends to be captured. Therefore, for example, when restoration processing is performed on a red component and a spectral component other than the red component based on spread functions having different characteristics, it is possible to further emphasize a part having a different color from the surrounding tissues such as a lesioned part. However, the above-described example is only an example. It should be noted that as long as it is possible to control an amount of blur for each spectral component, a spectral component serving as a target and content of the processing on a spread function corresponding to the spectral component are not necessarily limited to the above example.

The example of calculating a spread function according to a color of a subject has been described above with reference to FIG. 19 as Example 2-3.

Example 2-4: Control According to AF Control State

Next, as Example 2-4, an example of switching a spread function according to a control state (hereinafter simply referred to as an "AF control state") of focus point detection based on a predetermined AF method will be described.

The above-described examples have been described with a focus on cases in which control of AF is completed and a desired subject is in focus. On the other hand, in a situation in which a focus position is detected based on AF, a focus point position may be sequentially changed according to movement of each optical system (for example, a coupling optical system) and an amount of blur at positions in the captured image is also sequentially changed according to a change in the focus point position.

In view of such a situation, when a focus position is detected based on AF, for example, a spread function for controlling a depth of field to further increase may be applied. Detection of the focus position may be appropriately performed according to an instruction of the user (for example, from a button) or continuously performed regularly. When control information thereof is acquired, a spread function of increasing a depth of field may be applied. According to such control, even in a situation in which a focus point position is sequentially changed according to detection of the focus position, it is possible to identify the sample (the subject). However, the above-described example is only an example. It should be noted that as long as it is possible to control an amount of blur according to an AF control state, content of the processing is not necessarily limited to the above-described example. In addition, as long as it is possible to switch a spread function according to various control states, the control state is not necessarily limited to the AF control state. As a specific example, the spread function may be switched according to whether a magnification of the optical zoom is changed (that is, whether a control state of the optical zoom is changed).

The example of switching a spread function according to the AF control state has been described above as Example 2-4.

Example 2-5: Example of Control According to Observation Method

In the field of medical care, for example, according to a type of special light observation and a surgical procedure of surgery, a sample observation method differs and a characteristic of an image that is necessary for the observation also differs. Therefore, as Example 2-5, an example of calculating PSF information according to a difference of an observation method resulting from a difference in a type of special light observation and a surgical procedure of surgery will be described.

For example, as described above, in surgery to approach deep portions of the nose, ear and brain, since the surgical field is long and narrow, it is necessary to acquire an image having a broader depth of field in some cases. In such a case, for example, as in the operation in the blur reducing priority mode described above, PSF information is calculated based on a spread function $a(z)$ for assigning a weight according to a position in the depth direction (the z direction) such that a depth of field further increases, and the PSF information may be applied to restoration processing.

In addition, as another example, in surgery in which a finer procedure is necessary, for example, in a case in which a treatment is performed on a blood vessel on a surface of the brain, it is necessary to acquire an image whose sense of resolution is better even if a depth of field is somewhat shallow. In such a case, for example, as in the operation in the focus priority mode described above, PSF information is calculated based on a spread function $a(z)$ for assigning a weight according to a position in the depth direction (the z direction) such that a subject at a focus position is presented more sharply, and the PSF information may be applied to restoration processing.

In addition, when near-infrared fluorescence observation is performed, an infrared component (IR) mainly serves as an observation target. In such a case, for example, PSF information is calculated based on a spread function $IR(\lambda)$ for assigning a weight mainly using the infrared component (IR) as a target and the PSF information may be applied to restoration processing.

In addition, orthopedic joint surgery is performed in water in some case. In a situation in which surgery is performed in water in this manner, since an image is captured in water, an image in which blur generally occurs tends to be acquired. Therefore, in such a case, for example, PSF information is calculated based on a spread function $a(z)$ for assigning a weight according to a position in the depth direction (the z direction) such that a depth of field further increases and the PSF information may be applied to restoration processing.

However, the above-described examples are only examples. As long as it is possible to acquire an image having a characteristic that is necessary according to a type of special light observation and a surgical procedure of surgery, a method of calculating a spread function and a method of calculating PSF information according to the spread function are not particularly limited.

The application example of a spread function for assigning a weight to PSF information according to a difference of an observation method resulting from a difference in a type of special light observation and a surgical procedure of surgery has been described above as Example 2-5.

Example 2-6: Example of Control According to Observation Target

Next, as Example 2-6, an example of calculating PSF information according to the observation target will be described. This description will mainly focus on an application example in the field of medical care.

For example, when an organ in an abdominal cavity or a thoracic cavity is used as an observation target and the organ is imaged in a relatively large size, a situation in which the entire organ is widely observed may be assumed. In such a case, for example, as in the operation in the blur reducing priority mode described above, PSF information is calculated based on a spread function $a(z)$ for assigning a weight according to a position in the depth direction (the z direction) such that a depth of field further increases, and the PSF information may be applied to restoration processing. Accordingly, for example, it is possible to acquire an image in which blur is reduced across the entire organ serving as the observation target. Decision of whether the organ is imaged in a relatively large size may be performed by an input of the user, or a certain organ may be decided based on, for example, image recognition, from characteristic points in the image. In addition, when areas in the image are divided according to colors and patterns and characteristics thereof differ, it may be decided that areas having different characteristics in the living body are imaged, that is, the entire organ is imaged largely.

In addition, as another example, when a blood vessel stream is a main observation target and the blood vessel stream is imaged across a wide area in the image, it is desirable that the blood vessel stream be imaged more sharply. In such a case, for example, as in the operation in the focus priority mode described above, PSF information is calculated based on a spread function a(z) for assigning a weight according to a position in the depth direction (the z direction) such that a subject at a focus position is presented more sharply, and the PSF information may be applied to restoration processing. Decision of whether a blood vessel stream is imaged across a wide area in an image may be performed by an input of the user or performed according to whether a continuously branched edge is imaged based on, for example, image recognition.

The switching of control according to the observation target described above may be automatically performed by, for example, the image processing device 510. As a specific example, the image processing device 510 performs so-called image analysis of the captured image, recognizes the observation target (subject) that is captured in the image, and may switch PSF information (or a spread function for calculating the PSF information) that is applied to restoration processing according to the recognized observation target.

In addition, the image processing device 510 may calculate PSF information that is applied to restoration processing and a spread function for calculating the PSF information based on, for example, an observation mode that is selected by the observer (the user) according to the observation target.

As an example of calculating PSF information according to the observation target, particularly, the application example in the field of medical care has been described above on focus as Example 2-6.

Example 2-7: Example of Control Related to Switching PSF Information

As described above, the image processing device 510 according to the present embodiment calculates a plurality of pieces of PSF information according to the condition related to observation of a sample (for example, the condition of the observation range) and can selectively apply at least a part of PSF information among the plurality of pieces of PSF information to restoration processing. Next, as Example 2-7, an example of control when PSF information is selectively switched will be described in connection with a specific application example. This description will mainly focus on an application example in the field of medical care.

Specifically, as described above, according to a type of special light observation and a surgical procedure of surgery, PSF information may be selectively switched. In such a case, based on an observation mode that is selected by, for example, the observer (the user), according to a type of special light observation and a surgical procedure of surgery, the image processing device 510 selects PSF information corresponding to the observation mode and may apply the selected PSF information to restoration processing.

In addition, a case in which, even while observation is performed, the mode is temporarily switched to another observation mode and then observation is performed may be assumed. As a specific example, a situation in which a sample is observed while observation of a general optical image and special light observation are appropriately switched may be assumed. Even in such a case, the image processing device 510 selects PSF information according to an observation mode that is selected by, for example, the observer (the user), and may apply the selected PSF information to restoration processing.

In addition, as described above, the image processing device 510 recognizes a state and situation related to observation of a sample based on, for example, an analysis result of the captured image, and may adaptively switch PSF information according to the recognition result of the state and situation.

On the other hand, there are cases in which an error may occur in the recognition of a state and a situation by the image processing device 510. For example, when the image processing device 510 responds sensitively to such a recognition error and PSF information is temporarily erroneously switched, a characteristic of an image that is presented to the observer is temporarily switched and observation of a sample is inhibited may be assumed. In view of such a situation, for example, a mechanism for suppressing PSF information from being switched according to a change in a short-term state and situation may be provided in the image processing device 510.

Figure 20:
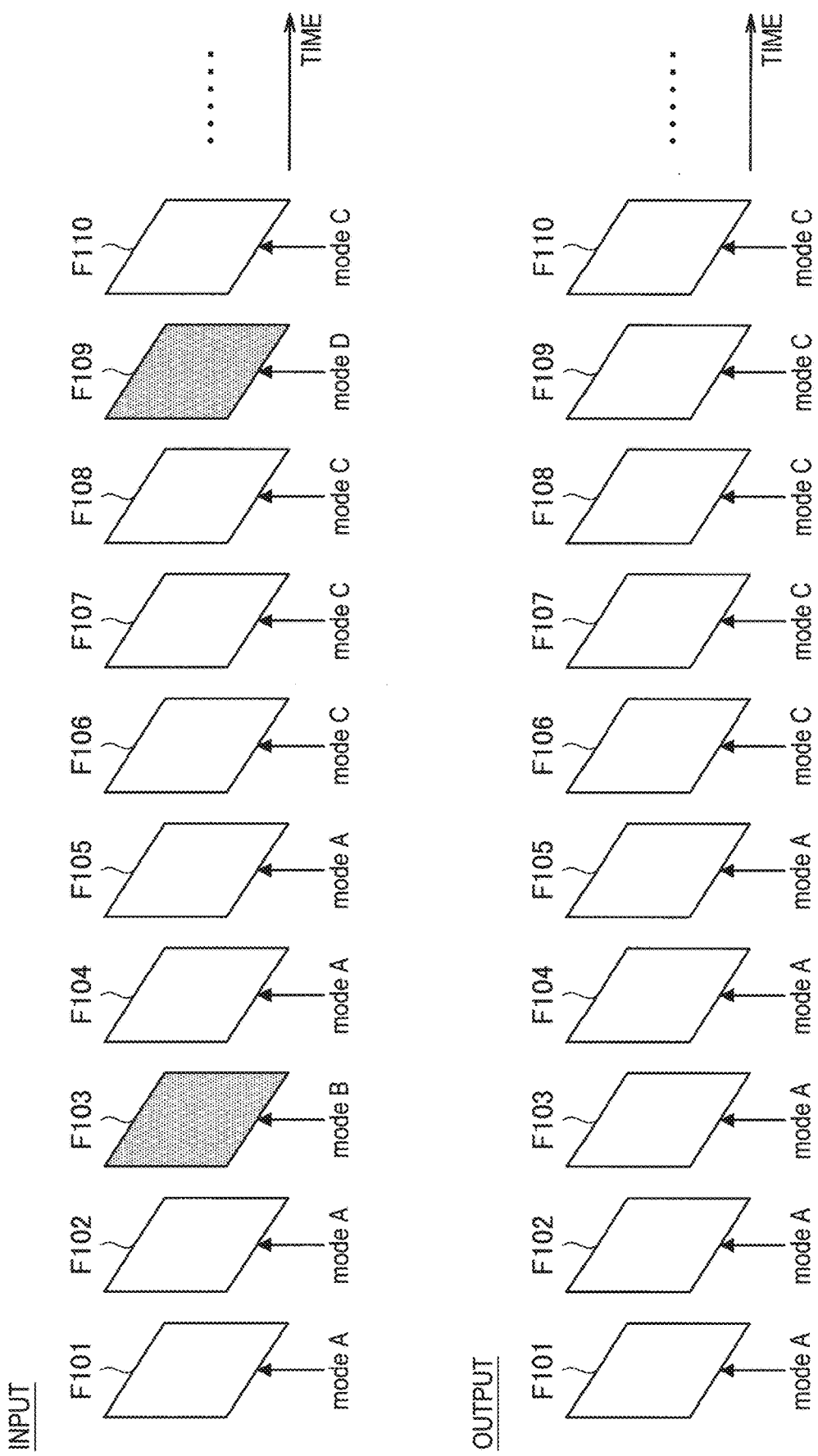
FIG. 20 is an explanatory diagram for describing an example of control related to switching PSF information by an image processing device according to Example 2-7.

For example, FIG. 20 is an explanatory diagram for describing an example of control related to switching PSF information by the image processing device 510 according to Example 2-7. In FIG. 20, reference signs F101 to F110 denote frames of a moving image acquired in time series. In addition, a mode A to a mode D denote different observation modes, and restoration processing in which different PSF information according to the observation mode is applied is applied to each of the frames.

In the example shown in FIG. 20, the image processing device 510 uses each of the frames as a sequential processing target and compares an observation mode (in other words, PSF information according to the observation mode) in the frame with an observation mode in a few frames before and after the frame. Then, the image processing device 510 detects a frame in which an observation mode is changed for a short term based on the comparison result of the observation modes between frames and suppresses PSF information in the frame from being switched.

For example, in FIG. 20, the upper drawing indicated by "input" schematically shows the series of frames F101 to F110 in time series and observation modes that are set in the frames before the control related to suppressing switching of PSF information described above is applied. For example, in the "input" side drawing, when the frames F101 to F105 are in focus, the observation mode is temporarily switched from the mode A to the mode B only in the frame F103. In addition, when the frames F106 to F110 are in focus, the observation mode is temporarily switched from the mode C to the mode D only in the frame F109. In such a case, for example, since PSF information applied to restoration processing is temporarily switched at timings of the frames F103 and F109, a characteristic of the image to be output is temporarily changed.

On the other hand, in FIG. 20, the lower drawing indicated by "output" schematically shows frames F101 to F110 and observation modes that are set in the frames when the control related to suppressing switching of PSF information described above is applied. Frames to which the same reference signs are attached at the "input" side and the "output" side indicate the same frames. For example, in the "output" side drawing, the observation mode in, for example, the frame F103, is corrected to the mode A to match those of previous and next frames and PSF information that is applied to restoration processing of the frame F103 is switched to PSF information corresponding to the mode A. Similarly, the observation mode in the frame F109 is corrected to the mode C to match those of previous and next frames and PSF information that is applied to restoration processing of the frame F109 is switched to PSF information corresponding to the mode C.

As a more specific example, the image processing device 510 extracts observation modes that are set in a frame serving as a processing target and in a few frames before and after the frame, and corrects an observation mode of the frame serving as a processing target to an observation mode that is set in more frames. According to such control, for example, it is possible to suppress PSF information from being switched according to a temporary (short-term) change in a state and situation resulting from, for example, a recognition error and it is possible for an image to be observed with less flickering.

However, the above-described example is only an example. As long as it is possible to suppress PSF information from being switched according to a temporary (short-term) change in a state and situation, content of the processing is not particularly limited. As a specific example, the image processing device 510 may correct the observation mode (or PSF information according to the observation mode) of the target frame to match that of a frame immediately before the frame. In addition, as another example, the image processing device 510 may apply PSF information having a smaller offset of changes in weighting or PSF information having a more intermediate characteristic within PSF information between frames that are adjacent to each other as PSF information corresponding to each of the frames.

The example of control when PSF information is selectively switched has been described above in connection with the specific application example, as Example 2-7.

5. HARDWARE CONFIGURATION

Figure 21:
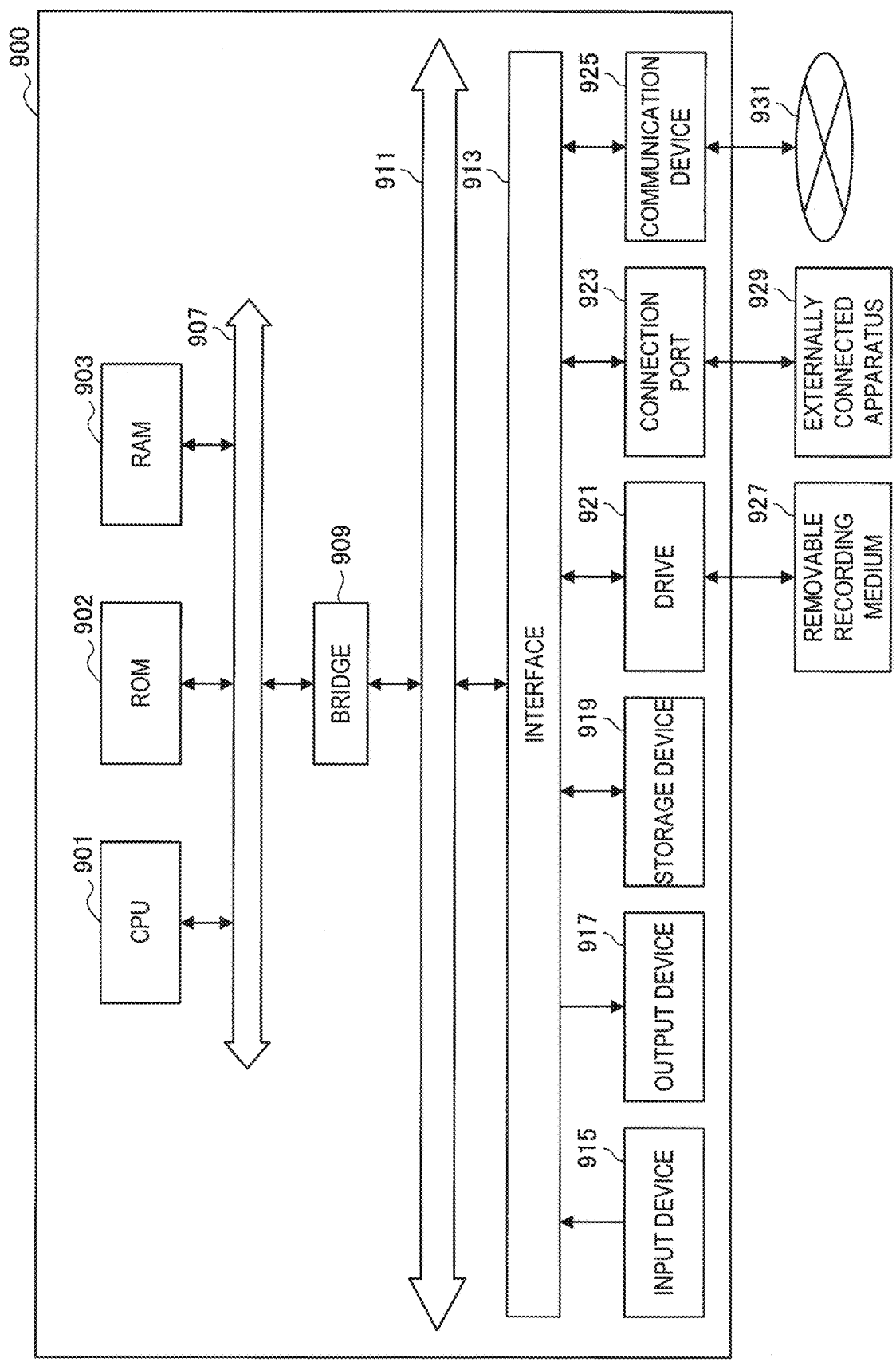
FIG. 21 is a functional block diagram showing a configuration example of a hardware configuration of an information processing apparatus of an endoscopic device according to the embodiment.

Next, a hardware configuration of an information processing apparatus 900 of a medical observation system (for example, the medical image processing system 1 shown in FIG. 1) according to the present embodiment such as the above-described CCU 51 (in other words, the image processing device) will be described in detail with reference to FIG. 21. FIG. 21 is a functional block diagram showing a configuration example of a hardware configuration of the information processing apparatus 900 of the medical image processing system 1 according to an embodiment of the present disclosure.

The information processing apparatus 900 of the medical image processing system 1 according to the present embodiment mainly includes a CPU 901, a ROM 903 and a RAM 905. In addition, the information processing apparatus 900 further includes a host bus 907, a bridge 909, an external bus 911, an interface 913, an input device 915, an output device 917, a storage device 919, a drive 921, a connection port 923 and a communication device 925.

The CPU 901 serves as an arithmetic processing device and a control device, and controls all or some operations in the information processing apparatus 900 according to various programs recorded in the ROM 903, the RAM 905, the storage device 919 or a removable recording medium 927. The ROM 903 stores programs and arithmetic parameters that are used by the CPU 901. The RAM 905 temporarily stores programs that are used by the CPU 901 and parameters that are appropriately changed when the programs are executed. These are connected to each other by the host bus 907 that includes an internal bus such as a CPU bus. The control unit 513, the weighting control unit 514, the PSF calculating unit 515, the selecting unit 516 and the image processing unit 517 described above with reference to FIG. 7 may be implemented by, for example, the CPU 901.

The host bus 907 is connected to the external bus 911 such as a peripheral component interconnect/interface (PCI) bus through the bridge 909. In addition, the input device 915, the output device 917, the storage device 919, the drive 921, the connection port 923 and the communication device 925 are connected to the external bus 911 through the interface 913.

The input device 915 is an operation means operated by a user, such as a mouse, a keyboard, a touch panel, buttons, a switch, a lever, and pedal. Also, the input device 915 may be a remote control means (a so-called remote control) using, for example, infrared light or other radio waves, or may be an externally connected device 929 such as a mobile phone or a PDA conforming to the operation of the information processing apparatus 900. Furthermore, the input device 915 generates an input signal based on, for example, information which is input by a user with the above operation means, and is configured from an input control circuit for outputting the input signal to the CPU 901. The user of the information processing apparatus 900 can input various data to the information processing apparatus 900 and can instruct the biometric authentication apparatus 10 to perform processing by operating this input apparatus 915.

The output device 917 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, and the like. For example, the output device 917 outputs a result obtained by various processings performed by the information processing apparatus 900. More specifically, the display device displays, in the form of texts or images, a result obtained by various processes performed by the information processing apparatus 900. On the other hand, the audio output device converts an audio signal such as reproduced audio data and sound data into an analog signal, and outputs the analog signal. The display device 53 described above with reference to FIG. 1 may be implemented by, for example, the output device 917.

The storage device 919 is a device for storing data configured as an example of a storage unit of the information processing apparatus 900 and is used to store data. The storage device 919 is configured from, for example, a magnetic storage device such as a HDD (Hard Disk Drive), a semiconductor storage device, an optical storage device, or a magneto-optical storage device. This storage device 919 stores programs to be executed by the CPU 901, various data, and various data obtained from the outside. The PSF storage unit 512 described above with reference to FIG. 7 may be implemented by, for example, the storage device 919.

The drive 921 is a reader/writer for recording medium, and is embedded in the information processing apparatus 900 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray (registered trademark) medium. The removable recording medium 927 may be a CompactFlash (CF; registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing devices to directly connect to the information processing apparatus 900. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (registered trademark) (High-Definition Multimedia Interface) port, and the like. By the externally connected apparatus 929 connecting to this connection port 923, the information processing apparatus 900 directly obtains various data from the externally connected apparatus 929 and provides various data to the externally connected apparatus 929.

The communication device 925 is a communication interface configured from, for example, a communication device for connecting to a communication network 931. The communication device 925 is, for example, a wired or wireless LAN (Local Area Network), Bluetooth (registered trademark), a communication card for WUSB (Wireless USB), or the like. Alternatively, the communication device 925 may be a router for optical communication, a router for ADSL (Asymmetric Digital Subscriber Line), a modem for various communications, or the like. This communication device 925 can transmit and receive signals and the like in accordance with a predetermined protocol such as TCP/IP on the Internet and with other communication devices, for example. The communication network 931 connected to the communication device 925 is configured from a network and the like, which is connected via wire or wirelessly, and may be, for example, the Internet, a home LAN, infrared communication, radio wave communication, satellite communication, or the like.

The example of the hardware configuration capable of implementing functions of the information processing apparatus 900 of the medical observation system according to an embodiment in the present disclosure has been described above. The respective components may be configured using a general purpose member or may be configured by hardware that is specialized for functions of respective components. Therefore, it is possible to appropriately change a hardware configuration to be used according to a technology level when the present embodiment is implemented. Although not shown in FIG. 21, it should be noted that various configurations corresponding to the information processing apparatus 900 of the medical observation system are included.

A computer program for implementing the functions of the information processing apparatus 900 of the medical observation system according to the present embodiment described above can be prepared and installed in a personal computer or the like. In addition, it is possible to provide a computer readable recording medium in which such a computer program is stored. Examples of the recording medium include a magnetic disk, an optical disc, a magneto optical disc and a flash memory. In addition, the computer program may be delivered via, for example, a network, without using the recording medium. In addition, the number of computers that execute the computer program is not particularly limited. For example, a plurality of computers (for example, a plurality of servers) may execute the computer program in cooperation.

6. CONCLUSION

As described above, in the medical image processing system 1 according to the present embodiment, the image processing device 510 calculates a function (psf) for controlling an amount of blur in the image in which a subject image is captured according to a condition related to observation of the subject image. Then, the image processing device 510 uses the image captured by the camera head 13 as an input image and performs restoration processing on the input image based on the calculated function. In such a configuration, according to the medical image processing system 1 in the present embodiment, it is possible to observe the observation target in a more suitable manner according to a state and situation related to observation of the subject image, for example, an observation environment condition and characteristics of a subject serving as the observation target.

In the example shown above, a case in which restoration processing is performed on the input image based on PSF information has been described. However, as long as it is possible to control an amount of blur in the input image (that is, reduce deterioration in the subject image), a function applied to the restoration processing is not necessarily limited to the PSF information. In addition, it should be noted that, as long as it is possible to control an amount of blur in the input image, content of the restoration processing is not limited.

In addition, this description has focused on a case in which the endoscope 10 is mainly configured as a rigid endoscope. However, an application target of the image processing device 510 according to the present embodiment is not necessarily limited to a medical image processing system for observing a sample through the rigid endoscope. As a specific example, the image processing device 510 may be applied to a medical image processing system for observing a sample through another medical observation device, for example, a flexible endoscope and a surgical microscope. In this case, when a psf is measured for each instrument such as various optical systems and imaging devices in each observation device, PSF information corresponding to the instrument may be acquired. It should be noted that, as long as a device or a system presents an image that is captured by the imaging device, an application target of the image processing device 510 according to the present embodiment is not necessarily limited to a medical system.

It should be understood by those skilled in the art that various modifications, combinations, sub-combinations and alterations may occur depending on design requirements and other factors insofar as they are within the scope of the appended claims or the equivalents thereof.

Further, the effects described in this specification are merely illustrative or exemplified effects, and are not limitative. That is, with or in the place of the above effects, the technology according to the present disclosure may achieve other effects that are clear to those skilled in the art based on the description of this specification.

(1)
A medical imaging system, including:
an image sensor;
a birefringent mask coupled to the image sensor; and
processing circuitry configured to
obtain image data from the image sensor, and
perform processing on the image data based on unique optical characteristics of a coupled medical device,
wherein the processing includes selecting at least one of depth of field expansion and blur improvement based on the unique optical characteristics.

(2)
The medical imaging system according to (1), wherein the processing uses one or more point spread functions (PSFs) extracted from a non-transitory memory, the non-transitory memory being configured to store a plurality of PSFs associated with the coupled medical device.

(3)
The medical imaging system according to (1)-(2), wherein the process includes selecting by giving priority to one of depth of field expansion and blur improvement.

(4)
The medical imaging system according to (1)-(3), further comprising:
a lens barrel.

(5)
The medical imaging system according to (1)-(4), wherein the image sensor is disposed within a camera head.

(6)
The medical imaging system according to (1)-(5), wherein the birefringent mask is disposed between the camera head and the lens barrel.

(7)
The medical imaging system according to (1)-(5), wherein the birefringent mask is incorporated into one of the lens barrel and the camera head.

(8)
The medical imaging system according to (1)-(5), wherein the birefringent mask is detachable from both the lens barrel and the camera head.

(9)
The medical imaging system according to (1)-(8), wherein the images are generated by giving priority to at least one of depth of the field expansion and the blur improvement based on a medical use of the imaging.

(10)
The medical imaging system according to (1)-(9), wherein the one or more point spread functions are selected based on an observation condition of a sample imaged by the image sensor.

(11)
The medical imaging system according to (1)-(10), wherein the observation condition includes type of light available for the medical imaging system.

(12)
The medical imaging system according to (1)-(11), wherein the stored plurality of PSFs associated with each medical device of a plurality of medical devices are generated at one of a time of manufacturing before sale, a time before surgery, and a time during surgery.

(13)
The medical imaging system according to (1)-(12), wherein the processing circuitry is further configured to generate the output images by being configured to select one of one or more modified point spread functions (PSFs) generated from the point spread functions (PSFs) extracted from the register.

(14)
The medical imaging system according to (1)-(13), where the modified point spread functions (PSFs) are generated by assigning a weight to the point spread functions (PSFs) extracted from the register.

(15)
The medical imaging system according to (1)-(14), wherein the weight is assigned based on a fineness of a sample.

(16)
The medical imaging system according to (1)-(14), wherein the weight is assigned based on a degree of focus.

(17)
The medical imaging system according to (1)-(14), wherein the weight is assigned based on a color of a subject.

(18)
The medical imaging system according to (17), wherein the weight is assigned to emphasize a red component when considering tissue.

(19)
The medical imaging system according to (1)-(13), wherein the processing circuitry is further configured to generate the output images by being configured to select one of the one or more modified point spread functions (PSFs) generated from the point spread functions (PSFs) extracted from the register based on an auto focus (AF) state or a manual focus state.

(20)
The medical imaging system according to (1)-(14), wherein the weight is assigned and/or one of the one or more modified point spread functions (PSFs) is selected based on an observation method.

(21)
The medical imaging system according to (20), wherein the weight is assigned and/or one of the one or more modified point spread functions (PSFs) is selected to prioritize depth of field when in water and when approaching deep portions of the nose, ear and brain, to improve blur when treatment is performed on a blood vessel on a surface of a brain, and to prioritize red frequencies when near-infrared fluorescence observation is being performed.

(22)
The medical imaging system according to (1)-(14), wherein the weight is assigned and/or one of the one or more modified point spread functions (PSFs) is selected based on an observation target.

(23)
The medical imaging system according to (22), wherein the weight is assigned and/or one of the one or more modified point spread functions (PSFs) is selected to prioritize depth of field when observing an organ in an abdominal cavity or a thoracic cavity and prioritize blur when observing a blood vessel stream.

(24)
The medical imaging system according to (22)-(23), wherein the observation target is determined based on user selection.

(25)
A medical image processing apparatus, including:
processing circuitry configured to
obtain image data from an image sensor having a birefringent mask coupled thereto, and
perform processing on the image data based on unique optical characteristics of a coupled medical device,
wherein the processing includes at least one of depth of field expansion and blur improvement based on the unique optical characteristics.

(26)
A medical image processing method, including:
obtaining image data from an image sensor having a birefringent mask coupled thereto;
performing processing on the image data based on unique optical characteristics of a coupled medical device, the processing including at least one of depth of field expansion and blur improvement based on the unique optical characteristics; and outputting the generated images.

(1a)
An image processing device including:
a control unit configured to perform control such that a correction image is generated based on an image in which a subject is captured and a function for adjusting an amount of blur in the image,
wherein the function is a function that is calculated according to a condition related to observation of the subject.

(2a)
The image processing device according to (1a),
wherein the function includes a plurality of functions having conditions that are different from each other, and
the control unit performs control such that the correction image is generated based on the function of at least any of the plurality of functions.

(3a)
The image processing device according to (1a),
wherein the condition related to the observation is detection information obtained from the image or an imaging condition of the image.

(4a)
The image processing device according to (3a),
wherein the detection information is color component information, edge information, contrast information or luminance information of the image.

(5a)
The image processing device according to (3a),
wherein the imaging condition is illumination light information, focus distance information, focus position information, focus control information, focus lens position information, optical zoom control information or optical zoom lens position information when the image is captured.

(6a)
The image processing device according to (2a),
wherein the control unit performs control such that a function to be applied is selected from among the plurality of functions according to the condition and the correction image is generated based on the function.

(7a)
The image processing device according to (6a),
wherein the function includes a plurality of functions that apply a weight according to the condition.

(8a)
The image processing device according to (6a),
wherein the function includes a plurality of functions that are calculated based on a spread function according to the condition.

(9a)
The image processing device according to any one of (1a) to (8a),
wherein the function is a point spread function.

(10a)
The image processing device according to (9a),
wherein a process of generating the correction image is deconvolution based on the point spread function.

(11a)
A medical image processing system including:
an imaging device that includes an imaging unit configured to capture an image of a sample and an optical system configured to form a subject image of the sample on the imaging unit; and
an image processing device configured to perform control such that a correction image is generated from an image that is captured by the imaging unit,
wherein the image processing device includes a control unit configured to generate a correction image based on the image and a function for adjusting an amount of blur in the image,
wherein the function is calculated according to a condition related to observation of the subject.

(12a)
The medical image processing system according to (11a),
wherein the imaging device is an endoscope in which at least a part of a lens barrel including the optical system is inserted into a body cavity of the sample.

(13a)
The medical image processing system according to (12a),
wherein the lens barrel is detachable from the imaging unit, and an optical element for controlling an amplitude transfer function of the optical system configured to form a subject image on the imaging unit is interposed between the lens barrel and the imaging unit,
wherein the function is a function that is calculated according to a characteristic of the optical element.

(14a)
The medical image processing system according to (13a),
wherein the optical element is held at an end side of the lens barrel, the end side being installed at the imaging unit.

(15a)
The medical image processing system according to (13a),
wherein the optical element is held at an end side at which the lens barrel of the imaging unit is installed.

(16a)
The medical image processing system according to (13a),
wherein the optical element is detachable from the imaging unit and the lens barrel.

(17a)
An image processing method including:
performing, by a processor, control such that a correction image is generated based on an image in which a subject is captured and a function for adjusting an amount of blur in the image,
wherein the function is a function that is calculated according to a condition related to observation of the subject.

(18a)
A recording medium having a program recorded thereon, the program causing a computer to perform control such that a correction image is generated based on an image in which a subject is captured and a function for adjusting an amount of blur in the image,
wherein the function is a function that is calculated according to a condition related to observation of the subject.

REFERENCE SIGNS LIST 1 endoscopic device
2 endoscope
3 imaging device
4 optical element
5 display device
6 light source device
7 light guide 8 transmission cable
9 camera head
10 image processing device
101 acquisition unit
102 storage unit
103 control unit
104 control unit
105 calculating unit
106 selecting unit
107 image processing unit

The invention claimed is:

1. A medical imaging system, comprising:
an image sensor;
a birefringent mask coupled to the image sensor; and
processing circuitry configured to
obtain image data from the image sensor,
select a point spread function including at least one of depth of field expansion and blur improvement from a plurality of point spread functions corresponding to unique optical characteristics of a coupled medical device, based on an observation mode, and
perform processing on the image data based on the point spread function, wherein,
in a normal light observation mode, a first point spread function (PSF) information is selected,
in a special light observation mode, a second PSF information, different from the first PSF information,
the first PSF information and the second PSF information is stored in a memory in association with the coupled medical device, and
the processing circuitry is configured to read different PSF information for each type of coupled medical device from the memory.

2. The medical imaging system according to claim 1, wherein the processing uses one or more point spread functions (PSFs) extracted from a non-transitory memory, the non-transitory memory being configured to store a plurality of PSFs associated with the coupled medical device.

3. The medical imaging system according to claim 1, wherein the special light observation mode is a mode in that a light source used for illumination emits light including near-infrared light as special light.

4. The medical imaging system according to claim 1, the first PSF information and the second PSF information are set based on a distribution function calculated for each spectral component of a light source used for illumination.

5. The medical imaging system according to claim 1, the processing circuitry is configured to select the second PSF information from a plurality of PSF information according to a type of the special light observation mode.

6. The medical imaging system according to claim 1, the processing circuitry is configured to perform different restoration processing for each frame by switching the point spread function selected for each frame of the respective image signal.

7. A medical imaging processor, comprising:
processing circuitry configured to
obtain image data from an image sensor coupled to a coupled medical device and to a birefringent mask,
select a point spread function including at least one of depth of field expansion and blur improvement from a plurality of point spread functions corresponding to unique optical characteristics of the coupled medical device, based on an observation mode, and
perform processing on the image data based on the point spread function, wherein,
in a normal light observation mode, a first point spread function (PSF) information is selected,
in a special light observation mode, a second PSF information, different from the first PSF information,
the first PSF information and the second PSF information is stored in a memory in association with the coupled medical device, and
the processing circuitry is configured to read different PSF information for each type of coupled medical device from the memory.

8. The medical imaging processor according to claim 7, wherein the special light observation mode is a mode in that a light source used for illumination emits light including near-infrared light as special light.

9. The medical imaging processor according to claim 7, the first PSF information and the second PSF information are set based on a distribution function calculated for each spectral component of a light source used for illumination.

10. The medical imaging processor according to claim 7, the processing circuitry is configured to select the second PSF information from a plurality of PSF information according to a type of the special light observation mode.

11. The medical imaging processor according to claim 7, the processing circuitry is configured to perform different restoration processing for each frame by switching the point spread function selected for each frame of the respective image signal.

12. An image processing method in a medical observation system, the method comprising:
obtaining image data from a camera head of a medical device, the camera head including an imaging sensor and a birefringent mask;
reading different PSF information for each type of coupled medical device from a memory in association with the coupled medical device,
selecting a point spread function including at least one of depth of field expansion and blur improvement from a plurality of point spread functions corresponding to unique optical characteristics of a coupled medical device, based on an observation mode, and
processing the image data based on the point spread function, wherein,
in a normal light observation mode, selecting a first point spread function (PSF) information, and
in a special light observation mode, selecting a second PSF information, different from the first PSF information.

13. The image processing method according to claim 12, further comprising performing different restoration processing for each frame by switching the point spread function selected for each frame of the respective image signal.

* * * * *